(12) United States Patent
Taylor et al.

(10) Patent No.: US 8,534,830 B2
(45) Date of Patent: *Sep. 17, 2013

(54) EYEGLASS WITH ENHANCED BALLISTIC RESISTANCE

(75) Inventors: Aaron Taylor, Hailey, ID (US); Jason Belbey, Fullerton, CA (US); Jeremy Hadden, Ketchum, ID (US); Neil Ferrier, Foothill Ranch, CA (US); Carlos D. Reyes, Rancho Santa Margarita, CA (US); Gardner Wade, San Clemente, CA (US)

(73) Assignee: Oakley, Inc., Foothill Ranch, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,216

(22) Filed: May 4, 2012

(65) Prior Publication Data

US 2012/0218504 A1 Aug. 30, 2012

Related U.S. Application Data

(63) Continuation of application No. 12/648,232, filed on Dec. 28, 2009, now Pat. No. 8,192,015.

(60) Provisional application No. 61/143,645, filed on Jan. 9, 2009, provisional application No. 61/266,804, filed on Dec. 4, 2009.

(51) Int. Cl.
*G02C 1/00* (2006.01)
*G02C 1/04* (2006.01)

(52) U.S. Cl.
CPC ... *G02C 1/04* (2013.01); *G02C 1/10* (2013.01)
USPC ............. 351/60; 351/106; 351/107; 351/154

(58) Field of Classification Search
CPC .................................... G02C 1/04; G02C 1/10
USPC .............. 351/41, 44, 60, 103–109, 140, 141, 351/154

See application file for complete search history.

(56) References Cited

U.S. PATENT DOCUMENTS 1,308,477 A 7/1919 Blanchard
2,652,746 A 12/1950 Shanks (Continued)

FOREIGN PATENT DOCUMENTS

EP 0121 018 10/1984
EP 0496 292 1/1991

(Continued)

OTHER PUBLICATIONS

Correspondence from the International Searching Authority in corresponding PCT Application No. PCT/US2010/020551, dated Nov. 5, 2010, 7 pages.

(Continued)

*Primary Examiner* — Huy K Mai

(74) *Attorney, Agent, or Firm* — Knobbe Martens Olson & Bear, LLP

(57) ABSTRACT

An eyeglass is provided that can comprise a frame, a lens, and at least one retention component that can secure the lens relative to the frame. The frame can be configured to support at least one lens in a field of view of a wearer. The frame can include a first ear stem and a second ear stem that allows the frame to be worn on the wearer's head. The at least one retention component can be supported by the frame and/or the lens and can be movable or fixed relative to the frame and/or the lens. The retention component can engage an engagement portion of the frame and/or the lens for preventing the lens from separating from the frame in response to a ballistic event.

22 Claims, 16 Drawing Sheets

(56) References Cited

U.S. PATENT DOCUMENTS

| | | |
|---|---|---|
| 2,610,323 A | 9/1952 | Johnson |
| 3,214,767 A | 11/1965 | Weber |
| 3,229,303 A | 1/1966 | Jonassen |
| 3,395,964 A | 8/1968 | Chartrice |
| 3,552,840 A | 1/1971 | Braget |
| 3,691,565 A | 9/1972 | Galonek |
| 3,826,564 A | 7/1974 | Werling, Sr. |
| 3,931,646 A | 1/1976 | Loughner |
| 4,056,853 A | 11/1977 | Bottazzini et al. |
| 4,176,921 A | 12/1979 | Matthias |
| 4,264,987 A | 5/1981 | Runckel |
| 4,314,814 A | 2/1982 | Deroode |
| 4,340,282 A | 7/1982 | Murakami |
| 4,357,080 A | 11/1982 | Solomon |
| 4,471,496 A | 9/1984 | Gardner, Jr. et al. |
| 4,515,448 A | 5/1985 | Tackles |
| 4,662,966 A | 5/1987 | Sumi et al. |
| 4,670,084 A | 6/1987 | Durand |
| 4,686,712 A | 8/1987 | Spiva |
| 4,759,622 A | 7/1988 | Schmidthaler |
| 4,813,775 A | 3/1989 | Kaksonen |
| 4,822,158 A | 4/1989 | Porsche |
| 4,859,048 A | 8/1989 | Jannard |
| 4,867,550 A | 9/1989 | Jannard |
| 4,983,030 A | 1/1991 | Chandler |
| 5,016,293 A | 5/1991 | Lickle |
| 5,048,944 A | 9/1991 | Porsche |
| 5,069,541 A | 12/1991 | Holmes et al. |
| 5,182,586 A | 1/1993 | Bennato |
| 5,182,587 A | 1/1993 | Hyoi |
| 5,208,614 A | 5/1993 | Jannard |
| 5,257,050 A | 10/1993 | Wiedner |
| 5,308,426 A | 5/1994 | Claveau |
| 5,357,292 A | 10/1994 | Wiedner |
| 5,373,331 A | 12/1994 | Vallalla et al. |
| 5,390,369 A | 2/1995 | Tubin |
| 5,400,089 A | 3/1995 | Danloup et al. |
| 5,410,763 A | 5/1995 | Bolle |
| 5,455,639 A | 10/1995 | Magdelaine et al. |
| 5,536,828 A | 7/1996 | Deluca et al. |
| 5,541,674 A | 7/1996 | Jannard |
| 5,576,775 A | 11/1996 | Bolle |
| 5,583,583 A | 12/1996 | Wilson |
| 5,587,747 A | 12/1996 | Bernheiser |
| 5,617,588 A | 4/1997 | Canavan et al. |
| 5,641,372 A | 6/1997 | Okuno |
| 5,648,832 A | 7/1997 | Houston et al. |
| 5,689,323 A | 11/1997 | Houston et al. |
| 5,708,489 A | 1/1998 | Jannard |
| 5,790,230 A | 8/1998 | Sved |
| 5,798,017 A | 8/1998 | Claveau |
| 5,805,261 A | 9/1998 | Houston et al. |
| 5,815,235 A | 9/1998 | Runckel |
| 5,862,529 A | 1/1999 | Moodie |
| 5,898,469 A | 4/1999 | Wang |
| 5,971,536 A | 10/1999 | Chiu |
| 6,086,199 A | 7/2000 | Holland et al. |
| 6,106,116 A | 8/2000 | Houston et al. |
| 6,119,279 A | 9/2000 | Haslbeck |
| 6,193,367 B1 | 2/2001 | Lee |
| 6,224,209 B1 | 5/2001 | Chen |
| 6,250,756 B1 | 6/2001 | Jannard |
| 6,282,727 B1 | 9/2001 | Lindahl |
| 6,296,357 B1 | 10/2001 | Bof |
| 6,464,353 B1 | 10/2002 | Spindelbalker |
| 6,477,717 B1 | 11/2002 | Winefordner et al. |
| 6,533,412 B1 | 3/2003 | Wang et al. |
| 6,550,912 B2 | 4/2003 | Vitaloni |
| 6,561,647 B1 * | 5/2003 | Chen ........................... 351/103 |
| 6,715,157 B2 | 4/2004 | Mage |
| 6,732,383 B2 | 5/2004 | Cleary et al. |
| 6,742,890 B1 | 6/2004 | Teng |
| 6,742,891 B2 | 6/2004 | Chen |
| 6,804,835 B2 | 10/2004 | Chou |
| 6,834,951 B2 | 12/2004 | Xie |
| 6,863,395 B1 | 3/2005 | Teng |
| 6,923,537 B2 | 8/2005 | Hartley et al. |
| 6,926,404 B2 | 8/2005 | Bassahon et al. |
| 6,929,364 B1 | 8/2005 | Jannard |
| 6,959,988 B1 | 11/2005 | Sheldon |
| 6,964,477 B1 | 11/2005 | Teng |
| 7,090,346 B2 | 8/2006 | Tsai |
| 7,137,426 B2 | 11/2006 | Neri et al. |
| 7,150,525 B1 | 12/2006 | Yang |
| 7,200,875 B2 | 4/2007 | Dondero |
| 7,219,992 B1 | 5/2007 | Wu |
| 7,219,993 B1 | 5/2007 | Chiou |
| 7,222,958 B1 | 5/2007 | Chiou |
| 7,222,959 B2 | 5/2007 | Jannard |
| 7,241,007 B2 | 7/2007 | Cody |
| 7,267,737 B2 | 9/2007 | Neri et al. |
| 7,328,999 B2 | 2/2008 | Zelman |
| 7,390,086 B2 | 6/2008 | Lee |
| 7,396,124 B1 | 7/2008 | Wang |
| 7,425,065 B2 | 9/2008 | Wang |
| 7,452,069 B2 | 11/2008 | Lipawsky |
| 7,481,529 B1 | 1/2009 | Chen |
| 7,497,569 B2 | 3/2009 | Webb |
| 7,520,217 B2 | 4/2009 | Roberts et al. |
| 7,553,013 B2 | 6/2009 | Tsai |
| 7,563,341 B2 | 7/2009 | Ferguson et al. |
| 7,585,072 B1 | 9/2009 | Wang-Lee |
| 7,681,257 B1 | 3/2010 | Broersma |
| D616,485 S | 5/2010 | Thixton |
| 7,712,894 B2 | 5/2010 | Tsai |
| 7,712,896 B1 | 5/2010 | Lee |
| 7,725,959 B2 | 6/2010 | Wang-Lee |
| D622,303 S | 8/2010 | Thixton |
| 7,810,174 B2 | 10/2010 | Matera |
| 7,856,673 B2 | 12/2010 | Reed |
| 7,887,181 B1 | 2/2011 | Chen |
| 7,954,942 B2 | 6/2011 | Calilung et al. |
| D649,178 S | 11/2011 | Moritz |
| D653,697 S | 2/2012 | Taylor |
| D653,698 S | 2/2012 | Taylor |
| 8,192,015 B2 * | 6/2012 | Taylor et al. ........................... 351/60 |
| 2002/0039928 A1 | 4/2002 | Spurgeon et al. |
| 2004/0141147 A1 | 7/2004 | Cyr |
| 2005/0070434 A1 | 3/2005 | Drake |
| 2005/0132478 A1 | 6/2005 | Canavan |
| 2006/0179554 A1 | 8/2006 | Barton |
| 2006/0191062 A1 | 8/2006 | Matera |
| 2006/0283555 A1 | 12/2006 | Green |
| 2007/0024806 A1 | 2/2007 | Blanshay |
| 2007/0121059 A1 | 5/2007 | Chiou |
| 2007/0200997 A1 | 8/2007 | Jannard |
| 2007/0240812 A1 | 10/2007 | Bortolato |
| 2007/0261782 A1 | 11/2007 | Frye et al. |
| 2008/0036961 A1 | 2/2008 | Zhou |
| 2008/0137028 A1 | 6/2008 | Webb |
| 2008/0155736 A1 | 7/2008 | Paulson et al. |
| 2008/0198323 A1 | 8/2008 | Siu |
| 2008/0266515 A1 | 10/2008 | Hou |
| 2008/0301858 A1 | 12/2008 | Wang-Lee |
| 2008/0304005 A1 | 12/2008 | DiChiara |
| 2009/0019620 A1 | 1/2009 | Reed |
| 2009/0038059 A1 | 2/2009 | McNeal et al. |
| 2009/0300830 A1 | 12/2009 | Mage |
| 2009/0313746 A1 | 12/2009 | Wang |
| 2010/0085533 A1 | 4/2010 | Calilung et al. |
| 2010/0231850 A1 | 9/2010 | Hones |
| 2011/0194065 A1 | 8/2011 | Belbey et al. |
| 2011/0225709 A1 | 9/2011 | Saylor et al. |
| 2011/0225710 A1 | 9/2011 | Reyes et al. |
| 2011/0225711 A1 | 9/2011 | Reyes et al. |
| 2011/0299026 A1 | 12/2011 | Calilung et al. |
| 2012/0038879 A1 | 2/2012 | Reyes et al. |

FOREIGN PATENT DOCUMENTS

| | | |
|---|---|---|
| EP | 1830221 | 9/2007 |
| FR | 1126329 | 11/1956 |
| FR | 2088866 | 1/1972 |
| FR | 2626683 | 8/1989 |
| FR | 2688322 | 12/1992 |

| FR | 2684292 | 6/1993 |
| GB | 512419 | 9/1939 |
| GB | 2278459 | 11/1994 |
| JP | 219021 | 2/1990 |
| WO | WO 98/30930 | 7/1998 |
| WO | WO 2007/049070 | 5/2007 |

OTHER PUBLICATIONS

International Search Report and Written Opinion issued in corresponding PCT Application No. PCT/US2010/020551, dated Aug. 3, 2010 in 20 pages.

International Preliminary Report on Patentability and Written Opinion of the International Searching Authority in corresponding PCT Application No. PCT/US2010/020551, dated Jul. 12, 2011 in 11 pages.

Invitation to Pay Additional Fees and, Where Applicable, Protest Fees in related International Application No. PCT/US2012/020211, mailing date of Mar. 26, 2012, in 4 pages.

International Search Report and Written Opinion in related International Application No. PCT/US2012/020211, mailing date of May 25, 2012, in 18 pages.

U.S. Appl. No. 13/020,747, filed Feb. 3, 2011.
U.S. Appl. No. 13/209,039, filed Aug. 12, 2011.
U.S. Appl. No. 13/051,913, filed Mar. 18, 2011.
U.S. Appl. No. 13/051,896, filed Mar. 18, 2011.
U.S. Appl. No. 13/051,889, filed Mar. 18, 2011.
U.S. Appl. No. 13/154,209, filed Jun. 6, 2011.

* cited by examiner

EYEGLASS WITH ENHANCED BALLISTIC RESISTANCE

CROSS-REFERENCE TO RELATED APPLICATIONS

This application is a continuation of U.S. application Ser. No. 12/648,232, filed on Dec. 28, 2009, which claims the benefit of U.S. Provisional Application Nos. 61/143,645, filed Jan. 9, 2009, and 61/266,804, filed on Dec. 4, 2009, the entireties of both of which are incorporated herein by reference.

BACKGROUND

1. Field of the Inventions

The present inventions relate generally to mounting systems for eyewear, and more specifically to methods and apparatuses for mounting an optical lens in a manner that provides excellent ballistic resistance and lens stability.

2. Description of the Related Art

A wide variety of improvements have been made in recent years in the eyewear field, particularly with respect to eyewear intended for use in active sports or as fashion sunglasses. These eyewear designs accomplish a variety of functional advantages, such as maximizing interception of peripheral light, reducing optical distortion and increasing the wearer's comfort level, compared to previous active sport eyewear.

Moreover, various other improvements have been made to enhance the durability and strength of eyeglasses. For example, various durable eyeglass designs have been developed that enable eyeglasses to be sturdy even during accidents, impact, stress, and other forms of use or misuse. Further, lenses have also been developed that have enhanced ballistic protection. Thus, an eyeglass can be generally resistant to breaking, bending, or otherwise becoming unusable.

SUMMARY

A continuing objective in the field of high quality eyewear, particularly that is intended for use in high-speed action sports or military applications, is providing eyewear that exhibits superior ballistic resistance and lens stability. Various improvements have been made that enable a wearer to quickly modify their eyeglass using replaceable components and/or lenses, such by using the systems disclosed in U.S. Pat. Nos. 4,730,915, 5,387,949, and 7,347,545, the entirety of the disclosure of each of which is incorporated herein by reference. Nevertheless, at least one of the embodiments disclosed herein reflects the realization that in order to enhance the ballistic resistance and lens stability of an eyeglass, additional support can be provided to a replaceable or removable lens.

Embodiments disclosed herein provide, at least in part, a durable eyeglass design that enables the lens on the eyeglass to be more securely retained by the frame of the eyeglass. The eyeglass can incorporate one or more retention components that may be used in conjunction with traditional lens mounting components, such as those in the systems disclosed in the patent references mentioned above. However, in some embodiments, the retention components can be used independent of traditional lens mounting components.

In some embodiments, in response to a ballistic event (such as an impact from a projectile and/or blunt contact with an object), the retention component can advantageously constrain the lens from translational and/or rotational movement in all directions where the lens is engaged and/or supported by the retention component. Such a feature can be contrasted with prior art lens mounting components in that a prior art lens is generally constrained from translational and/or rotational movement in many, but not all directions at a given point along the lens-frame border. Thus, impact from a ballistic event can cause the prior art lens to be dislodged, dislocated, or dismounted from the prior art eyeglass frame.

For example, conventional detachable unitary lens systems include an upper frame having a downwardly facing lens groove. The upper edge of a lens is positioned within the lens groove. The lens is retained within the groove by a first interference fit at a first lateral edge of the lens, and a second interference fit at a second lateral edge of the lens. This may provide secure mounting of the lens and good resistance to motion of the lens from side to side relative to the frame during light use of the eyeglass. However, at least the center portion of the lens can be advanced downwardly and out of the lens groove during elastic reconfiguration of the eyeglass following impact. Thus, at least one of the embodiments disclosed herein reflects the realization that prior art eyeglasses fail to provide sufficient ballistic resistance.

In contrast, embodiments disclosed herein can securely retain the lens relative to the frame during and after a ballistic impact. For example, the center portion of the lens can be fully seated within the lens groove during and following impact.

Such embodiments can be advantageous in that they allow the lens to be securely retained by the frame without undermining or ruining the optical characteristics of the lens. For example, the lens can be secured to and/or supported by the frame in a manner that preserves the as-molded geometry of the lens.

Moreover, embodiments disclosed herein can advantageously provide an eyeglass in which the lens can be easily removed and replaced by the wearer while enabling the wearer to mount the lens such that the lens exhibits superior ballistic resistance and the lens stability.

For example, in some embodiments disclosed herein, an eyeglass is provided that comprises a frame onto which at least one lens can be mounted. The eyeglass can comprise at least one retention component. The retention component can be mounted onto, carried, or supported by the frame and/or a lens. The retention component can be configured to engage at least a portion of the frame and/or a lens. The retention component can be configured to secure the lens relative to the frame to prevent the lens from separating from the frame in response to a ballistic event. For example, the lens may "separated" from the frame when any portion of the upper edge of the lens is pulled out of the lens groove.

The retention component can comprise at least one engagement structure for facilitating engagement with the lens. Further, the retention component can be a system or plurality of components that operate to engage the lens.

In some embodiments, the retention component can comprise at least one clip. The clip can be attached along the frame. The clip can be disposed at a central portion and/or lateral portion(s) of the frame, such as centered on the midline of the frame. The clip can be actuated by the wearer in order to secure a central and/or a lateral portion(s) of the lens to the frame.

For example, the frame can comprise opposing lateral terminals that interconnect with corresponding projections or detents in the lens in order to mount the lens to the frame in a mounted position while a single clip is used to secure the center portion of the lens to the frame in order to prevent the lens from separating from the frame in response to a ballistic event. Thus, should the eyeglass be subjected to unexpected forces such as would result from being dropped, knocked, or hit by a projectile, the lens will not tend to be separate from the frame. However, multiple clips can also be used to secure the lens relative to the frame along a plurality of portions of points of the lens.

In some embodiments, the clip can be rotated relative to and/or about the frame and/or the lens. In some embodiments, the clip can be translated or slid relative to the frame and/or the lens. For example, the retention component can comprise a rotating or translating clip that can be mounted on or supported by the frame of the eyeglass. In some embodiments, the retention component can comprise a rotating or translating clip that can be mounted on, carried, or supported by the lens. The clip can be manually adjusted or actuated by the wearer. The clip can engage directly or indirectly with a portion of the frame and/or the lens. In some embodiments, one or more clips can engage directly or indirectly with a portion of a plurality of lenses, such as a dual lens system.

In some embodiments, the clip can comprise an engagement structure such as a tab that is operative to engage and/or interlock with an engagement portion or corresponding surface structure such as a recess or aperture on the frame and/or the lens.

For example, the lens can comprise an aperture or slot that can be engaged and/or supported by the tab of the clip. In some embodiments, the clip can have a first rotational/translational position or disengaged position in which the lens can be freely removed downwardly from the frame, enabling disengagement of the lens. The clip can also have a second rotational/translational position or engaged position in which the lens can be secured and/or supported relative to the frame such that the lens does not separate from the frame in response to a ballistic event.

The clip can have a hingeless configuration. For example, the clip can be configured as a tubular member that wraps around at least a portion of the frame. The clip can have a hingeless, rotatable configuration in which the clip rotates relative to or about at least a portion of the frame to facilitate engagement of the lens relative to the frame. The clip can also have a hingeless, translatable configuration in which the clip translates along at least a portion of the frame to facilitate engagement of the lens relative to the frame.

In some embodiments, the clip can be configured as a split ring having a gap or split. The split ring can encompass or surround a portion of the frame by wrapping around, for example, at least about 50% and/or less than or equal to about 80% of the perimeter or circumference of the portion of the frame, with approximately at least about 20% and/or less than or equal to about 50% of the clip defining the gap or split. In a rotating clip embodiment, the gap or split can be configured such that at least a portion of the lens can be received therein for securing the lens relative to the frame. In such embodiments, the tab can be disposed at one of the free ends forming the gap or split.

In some embodiments, a translating clip embodiment can engage a slot in the lens. For example, the lens can be seated against the frame with the clip being positioned adjacent to the slot of the lens in a first translational position or disengaged position. The clip can then be translated within the slot towards a second translation position or engaged position, thus securing the lens relative to the frame.

In some embodiments, the clip can be configured to snap-fit onto the frame. The clip can be urged onto the frame with a portion of the frame passing through the gap or split in the clip. In some embodiments, the clip can be fabricated from a resilient material such that the clip deflects to allow enlargement of the gap or split such that the clip can attach to the frame. The clip can therefore be attachable to the frame without requiring pins, latches, or other components. Embodiments disclosed herein can thus allow for superior assembly and maintenance of the eyeglass compared to other designs. Further, the design can be durable and sturdy, providing capable and secure retention despite stresses or other forces that may act on the eyeglass.

Further, the clip can rotate with the gap or split being moved from a first rotational position or disengaged position in which a portion of the lens can be received into the gap or split to a second rotation position or engaged position in which the gap or split is rotated such that the clip engages a portion of the lens. Rotation of the gap or split can enable quick and secure engagement with the lens.

In some embodiments, the clip can define an outer profile that tapers and blends with the surface of the frame. For example, the clip can define a contour or external shape that blends with a contour or external shape of the frame. In some embodiments, the contour or external shape can blend in only one of the first or second rotational positions. For example, a mismatch in contour can provide a visible and tactile indication that the clip is in a disengaged position while the clip and frame have a generally uniform, smooth contour when the clip is in the engaged position.

In some embodiments, the clip can rotate and/or translate about a horizontal axis such that the tab moves in a generally anterior-posterior direction to engage the lens. For example, the tab can be rotated within a generally vertical anterior-posterior plane to align with the lens to engage the lens. Further, the tab can be translated along the frame upon translation of the clip within a generally vertical anterior-posterior plane to align with the lens to engage the lens.

In some embodiments, the clip can rotate and/or translate about a vertical axis. In such embodiments, the tab can be rotated within a generally horizontal plane to align with the lens in a generally vertical plane to engage the lens.

For example, the engagement structure of the retention component can comprise a tab that is pivotally coupled to the frame such that the tab can rotate about a vertical axis. Optionally, the retention component can comprise a shaft that couples the retention component to the frame. Further, the retention component can optionally comprise an actuating element that is in mechanical communication with the tab such that the actuating element can be used to rotate the tab.

In some embodiments, the frame can comprise a recess or aperture configured to receive and/or support the retention component. For example, the recess or aperture of the frame can support the retention component such that a force (exerted in at least one direction) on the retention component is transferred to the frame. The recess or aperture of the frame can optionally be configured to support the retention component such that forces exerted in several directions on the retention component are transferred to the frame.

For example, in embodiments wherein the retention component rotates and/or translates about a horizontal axis, the retention component can engage with a horizontal section of the frame. As noted above, the engagement can be a snap-fit engagement. The retention component can fit over the horizontal section and rotate about the horizontal section. Further, the retention component can be weaved into or fit within a horizontally-extending recess or space in the frame.

Additionally, in embodiments wherein the retention component rotates and/or translates about a vertical axis, the retention component can engage with a vertical section of the frame. For example, the retention component can fit over the vertical section and rotate about the vertical section. Further, the retention component can be weaved into or fit within a vertically-extending recess or space in the frame.

The retention component can also comprise a plurality of clips disposed along the frame of the eyeglass. In such embodiments, the frame of the eyeglass can be configured with or without opposing terminals that are used to engage projections or detents of the lens in order to mount the lens in a mounted position. For example, the plurality of clips can be used as the sole connectors to mount and secure the lens from separating from the frame.

Furthermore, the retention component can be formed separately from the frame. For example, the retention component can be coupled to the frame and rotatable or slideable with respect to the frame. In some embodiments, the retention component can be advanced from a first orientation (or a disengaged position) to a second orientation (or an engaged position) in order to engage with the lens. For example, the frame and the retention component can also be configured to permit a predetermined range of rotational or axial movement of the retention component. In one embodiment, the frame can comprise one or more hardstop features that can enter with one or more corresponding detents or recesses in the retention component. The retention component can rotate in a given direction until a hardstop feature of the frame contacts a detents or recess of the retention component to restrict further rotation of the retention component.

For example, in embodiments in which the retention component comprises a hingeless clip, the clip can rotate between two or more rotational positions with hardstop features of the clip and the frame restraining motion of the clip at one or more of the positions. For example, the clip can be configured to comprise an interior having one or more protrusions or recesses that engage(s) with one or more protrusions or recesses of the frame. In some embodiments, the hardstop features can be hidden from view when in an assembled state. Further, engagement between the hingeless clip and the frame can also create the desired interaction between the corresponding hardstop features of the clip and the frame.

In addition, embodiments are provided in which the lens comprises an engagement portion that can be engaged and/or supported by the retention component. The engagement portion of the lens can comprise at least one of a recess, surface contour, cut-out, projection, slot, aperture, and other such surface structure formed in any variety of shapes and/or sizes. For example, in some embodiments, the engagement portion can be an aperture that extends through the thickness of the lens. The engagement structure can also be a cut-out that extends through the thickness of the lens and extends inwardly from a periphery of the lens. Further, some embodiments can be configured such that the frame comprises an engagement portion that can be engaged by a retention component that is supported by the lens.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION OF THE PREFERRED EMBODIMENT

Figure 1:
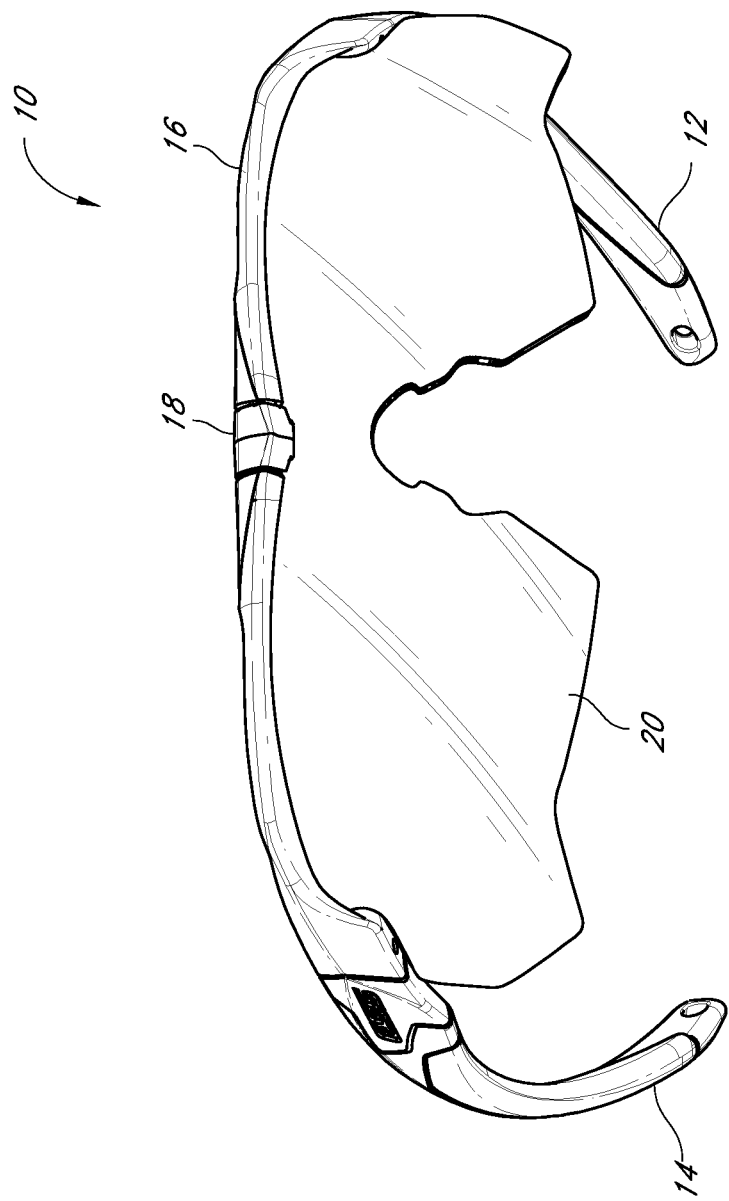
FIG. 1 is a perspective view of an eyeglass comprising a retention component for securing a lens to a frame of the eyeglass, in accordance with an embodiment of the present inventions.

While the present description sets forth specific details of various embodiments, it will be appreciated that the description is illustrative only and should not be construed in any way as limiting. Additionally, although particular embodiments of the present inventions may be disclosed or shown in the context of unitary or dual lens eyewear systems, such embodiments can be used in both unitary and dual lens eyewear systems. Further, although embodiments disclosed herein can be used with eyeglasses that have removable and replaceable lenses, embodiments are also contemplated in which the eyeglasses are not intended to provide for removable or replaceable lenses.

Further, although particular embodiments may be disclosed or shown in the context of frames having partial orbitals, such embodiments can be used with frames having both full and partial orbitals. Retention components and structures in accordance with embodiments disclosed herein can also be utilized to retain a lens or multi-lens construct within a goggle, such as a ski goggle or motocross goggle. The retention structures may be utilized either as the primary connector or as a secondary connector for cooperation with another lens retention system. Furthermore, various applications of such embodiments and modifications thereto, which may occur to those who are skilled in the art, are also encompassed by the general concepts described herein.

For example, some embodiments can provide an eyeglass comprising a frame and at least one retention component or structure. The frame can be configured to support at least one lens in a field of view of a wearer. The frame can comprise a first ear stem and a second ear stem. The frame can be worn on the wearer's head. The at least one retention component can be supported by the frame and/or by the at least one lens. The at least one retention component can be hingeless. The retention component can be movable relative to the frame and/or to the lens. The retention component can secure the at least one lens relative to the frame. For example, the retention component can engage an engagement portion of the lens for preventing the lens from separating from the frame in response to a ballistic event. Further, some embodiments can be configured such that the frame comprises an engagement portion that can be engaged by a retention component that is supported by the lens.

The retention component of the eyeglass can be configured to rotate relative to the frame and/or the lens to engage the respective one of the lens and/or the frame. The retention component can be permanently or detachably mounted on the frame and/or the at least one lens. The retention component can comprise a clip disposed at a central portion of the frame. The clip can be actuated by the wearer to secure a central portion of the lens to the frame. The retention component can be movable from a first orientation in which the lens can be freely moved relative to the frame to a second orientation in which the lens is secured relative to the frame.

For example, the retention component can rotate about a generally horizontal axis relative to the frame to engage the frame and/or the lens. Further, the retention component can comprise a rotatable clip mounted on the frame and/or lens. The rotating clip can comprise an engagement structure that is operative to engage the engagement portion of the lens and/or the frame.

The rotating clip can also comprise a generally tubular or cylindrical body, and the engagement structure can comprise an engagement tab extending generally circumferentially relative to the cylindrical body. The tubular or cylindrical body can be configured to engage a recess of the frame for mounting the retention component on the frame. The tab can have a first orientation in which the lens is movable relative to the frame and a second orientation in which the tab engages the lens to the secure the lens relative to the frame. For example, the tab of the clip can engage the lens at an angle of at least about 5 degrees and/or less than or equal to about 40 degrees relative to a horizontal plane. In some embodiments, the tab of the clip can engage the lens at an angle of about 19.2 degrees relative to a horizontal plane.

Additionally, the retention component can fit over a recess of the frame to be rotatable about a longitudinal axis of the frame. For example, the retention component can fit over the recess in a snap fit. In some embodiments, the engagement portion of the lens can comprise one of a recess and an aperture that can be engaged by the engagement structure of the rotating clip.

In other embodiments, the retention component can rotate about a generally vertical axis relative to the frame to engage the frame and/or the lens. For example, the retention component can comprise an actuation handle and at least one tab being rotatable upon rotation of the handle. The tab can extend generally transversely relative to the generally vertical axis. The tab can have a first orientation in which the lens is movable relative to the frame and a second orientation in which the tab engages the lens to the secure the lens relative to the frame. For example, the retention component can rotate in a plane that is generally coplanar with at least a portion of the lens. Additionally, the retention component can comprise an elongate shaft extending between the handle and the tab. Further, the frame can comprise a recess configured to receive at least a portion of the retention component to support the retention component relative to the frame. Furthermore, the handle can be accessible to the wearer for actuating the retention component.

In some embodiments, the frame can comprise opposing lateral terminals that interconnect with corresponding projections in the lens to mount the lens to the frame in a mounted position. The frame can comprise a lens groove. The lens groove can extend at least partially along the frame for receiving at least a portion of the lens therein.

In some embodiments, the at least one lens of the eyeglass can comprise an engagement portion. Further, the frame of the eyeglass can have a generally horizontal longitudinal axis and a pair of earstems extending posteriorly relative to the frame. The frame can be configured to support the at least one lens in the field of view of a wearer. Further, the eyeglass can be configured such that the at least one retention mechanism is coupled to the frame and rotatable about the longitudinal axis of the frame. The retention mechanism can comprise an engagement structure extending therefrom. The engagement structure can be moveable from a first orientation in which the lens can be freely moved relative to the frame to a second orientation in which the retention structure engages the engagement portion of the lens for securing the lens relative to the frame.

The frame can also comprise at least one stop element configured to limit the rotational orientation of the retention mechanism relative to the frame. The retention mechanism can also comprise at least one stop element corresponding to the at least one stop element of the frame. The stop elements can be configured to contact each other to limit the rotational orientation of the retention mechanism relative to the frame.

In some embodiments, the retention mechanism can comprise first and second stop elements that interact with the at least one stop element of the frame. The retention mechanism can have a variety of shapes and structural features, such as including a generally cylindrical body with the engagement structure extending generally circumferentially therefrom. For example, the at least one stop element of the retention mechanism can be formed along an interior surface of the retention mechanism. Further, the at least one stop element of the retention mechanism can comprise a recess, and the at least one stop element of the frame can comprise a protrusion.

The engagement structure of the retention mechanism can comprise a tab that engages the engagement portion of the lens at an angle of between about at least about 5 degrees and/or less than or equal to about 40 degrees relative to a line that is normal to the lens. Further, in some embodiments, the tab can engage the engagement portion of the lens at an angle of between at least about 10 degrees and/or less than or equal to about 20 degrees relative to a line that is normal to the lens. For example, the tab can engage the engagement portion of the lens at an angle of about 19.2 degrees.

With reference to FIG. 1, an embodiment of the present inventions is illustrated. In this embodiment, an eyeglass 10 is shown that comprises a pair of ear stems 12, 14, a frame 16, a retention component 18, and a lens 20. The eyeglass 10 illustrated in FIG. 1 is configured such that the lens 20 can be removed and replaced. However, in other embodiments, the lens may not be removable or replaceable. Nevertheless, such embodiments can provide increased lens stability and ballistic resistance, similar to the embodiment illustrated in FIG. 1.

Figure 2:
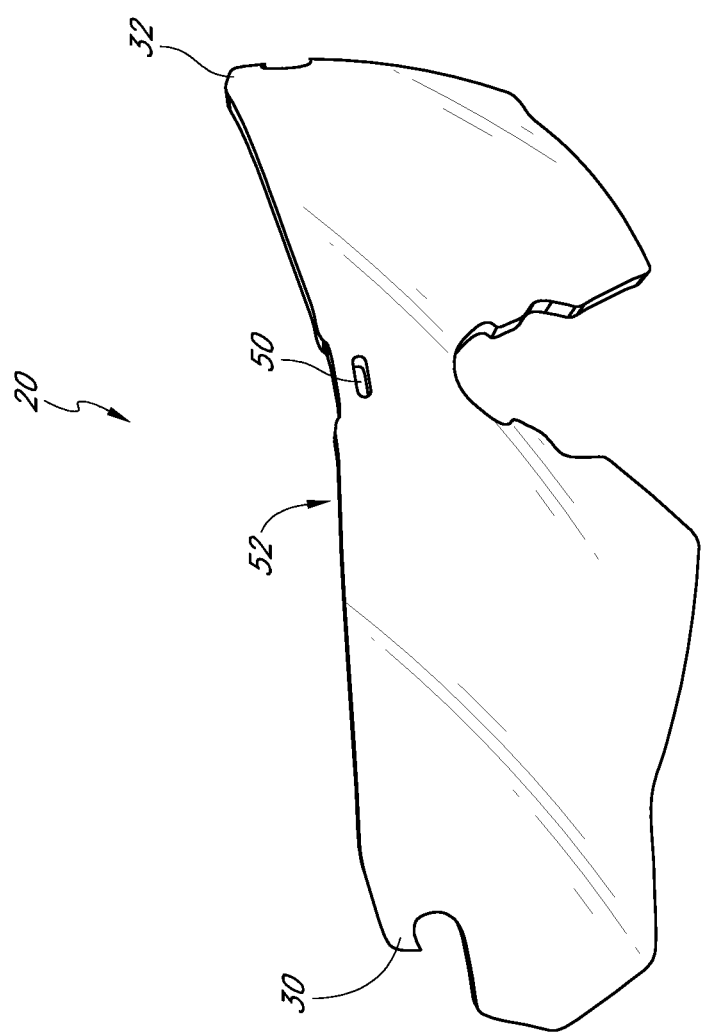
FIG. 2 is a perspective view of a lens comprising a slot that can be engaged by the retention component of the eyeglass shown in FIG. 1, according to an embodiment.
Figure 3:
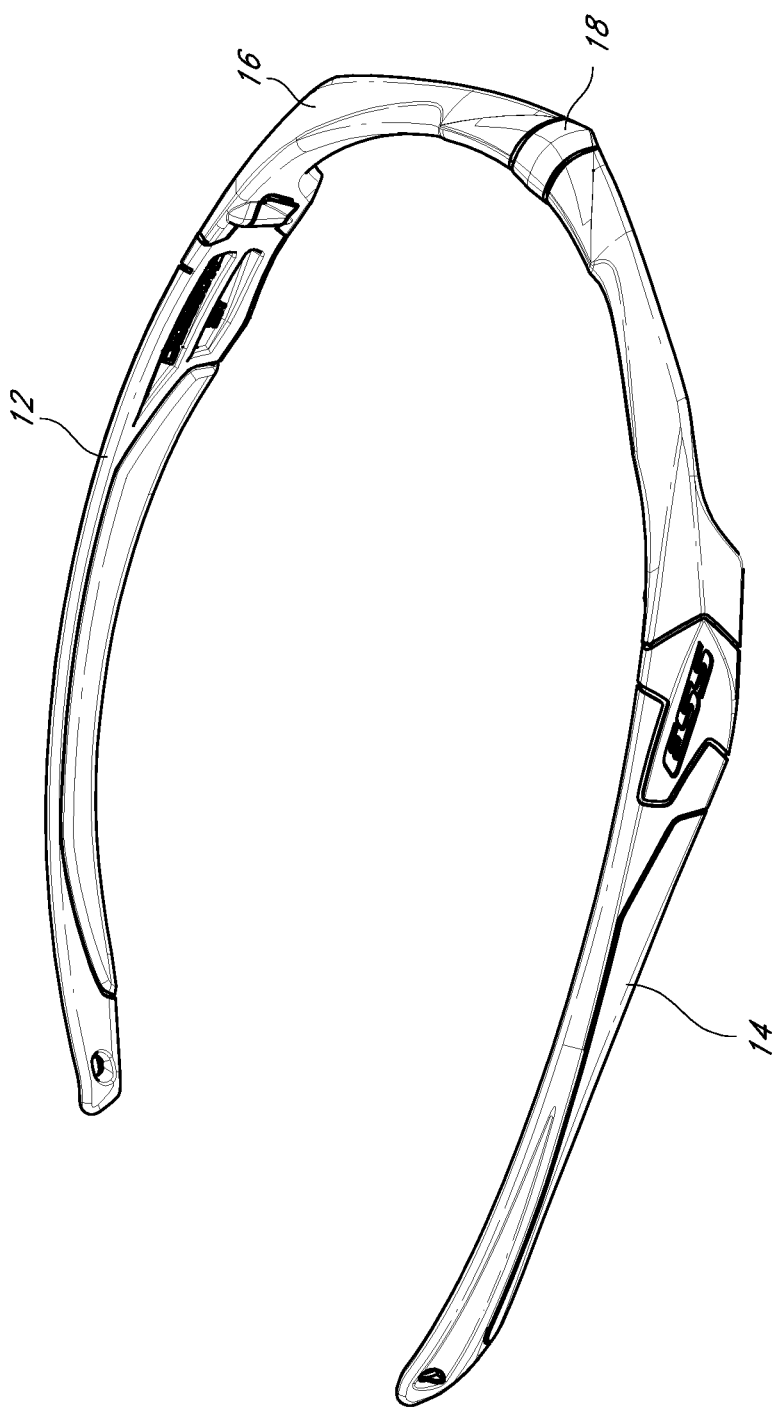
FIG. 3 is a top perspective view of the frame of the eyeglass shown in FIG. 1, according to an embodiment.

FIG. 2 illustrates an embodiment of the lens 20 for use with the eyeglass 10. The lens 20 can be configured to be supported by the frame 16. For example, the lens 20 can comprise one or more engagement portions that can be engaged with one or more retention components of the eyeglass for supporting the lens. Further, other structures can be used to support the lens. For example, the frame can comprise one or more opposing terminals and the lens can comprise one or more projections that can be fitted into the terminal(s) of the frame. However, the use of structures such as projections and terminals is optional and can be omitted in some embodiments. For example, structures in addition to the retention component(s) and engagement portion(s) may be unnecessary where two or more retention components and engagement portions are spaced apart along the edge of the lens.

As will be appreciated with reference to FIGS. 1-4, the lens 20 of the eyeglass 10 can be selectively removed and replaced by the wearer. For example, the wearer can replace the lens 20 with a lens having a different tint or shape. In some embodiments, the wearer can engage interlocking projections or detents of the lens 20 with corresponding opposing terminals of the frame 16 to remove and replace the lens 20.

Figure 4:
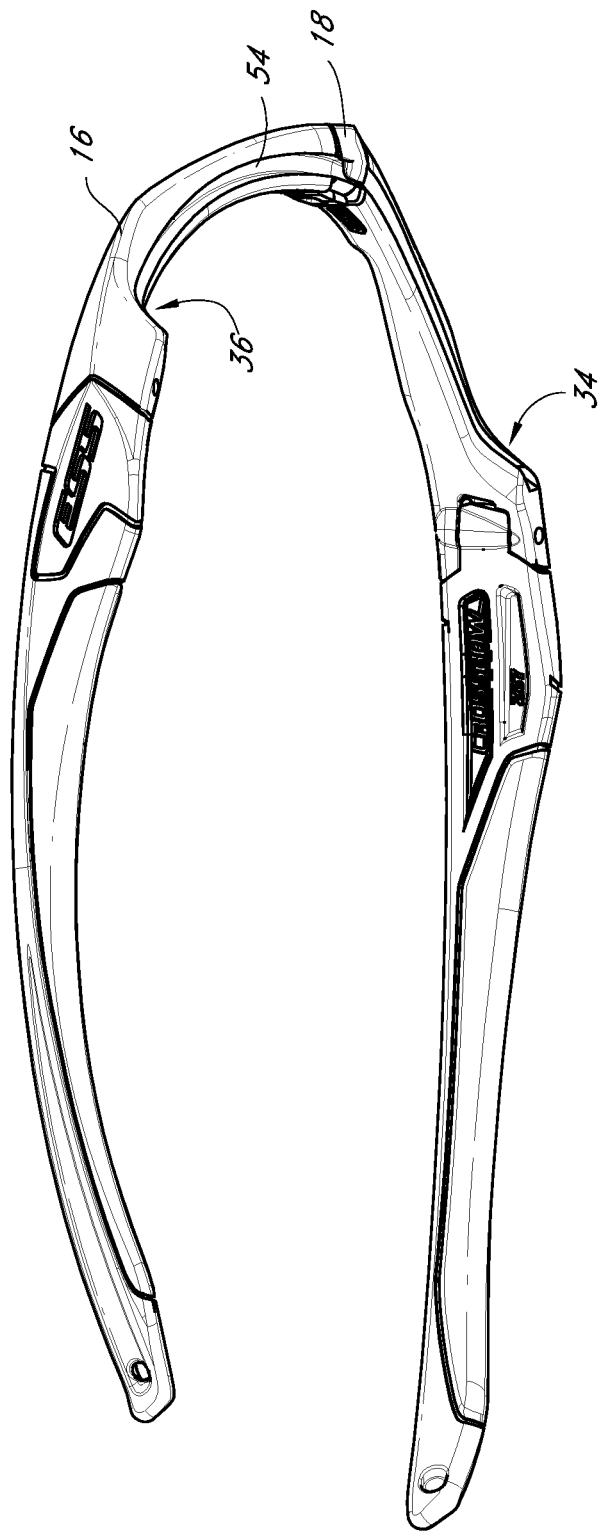
FIG. 4 is a bottom perspective view of the frame of the eyeglass shown in FIG. 1, according to an embodiment.

For example, as shown in FIGS. 2 and 4, the lens 20 can comprise a pair of projections 30, 32 that can be seated in corresponding terminal recesses 34, 36 of the frame 16. In use, when the projections 30, 32 are received within the terminal recesses 34, 36 of the frame 16, the lens 20 can be generally snap fitted into and retained within the lens groove 54 in the frame 16. Thus, in some embodiments, such an arrangement can provide a further degree of lens retention and stabilization in addition to that provided by the retention component.

In accordance with the embodiment shown in FIGS. 1-4, the lens 20 can also comprise an engagement portion or structure 50. The engagement portion 50 can comprise at least one portion of the lens 20 can be one of a recess, surface contour, cut-out, projection, slot, aperture, and other such surface structures and be formed in a variety of shapes and/or sizes. For example, in the illustrated embodiment, the engagement portion 50 is shown as an aperture that extends through the thickness of the lens 20. The engagement portion 50 is shown as a single aperture, but can be formed as a plurality of apertures. The engagement portion 50 can extend generally parallel relative to a line that is normal to the lens 20 (as shown for example, in FIG. 11A). Further, the engagement portion 50 can extend generally transversely relative to a line that is normal to the lens 20 (as shown for example, in FIG. 11B).

The engagement portion 50 can be disposed at any point along the lens 20, and preferably, at any point along the lens-frame boundary 52 of the lens 20. The lens-frame boundary can be defined as the portion or portions of the lens along which the lens and the frame border, overlap, or interconnect with each other. For example, referring to FIGS. 1-2, the lens-frame boundary 52 is generally the upper section of the lens 20, adjacent to the upper edge of the lens 20 that is seated within a groove 54 of the frame 16 (shown in FIG. 4). Thus, although a single engagement portion 50 is used in the embodiment of the lens 20 shown in FIG. 2, other embodiments of the lens 20 can be constructed that comprise two or three or four or more engagement portions 50 disposed along the lens-frame boundary 52.

Additionally, as mentioned above, although the engagement portion 50 is shown as an aperture, the engagement portion 50 can also comprise a protrusion, a detent, and/or other shapes and sizes of engagement portions that allow the lens 20 to be interconnected with the retention component 18. Furthermore, as noted above, the lens 20 can comprise a unitary or dual lens system. For example, one or more engagement portions can be used in each lens of a dual lens system, as desired. Moreover, the lens 20 can be mounted within an orbital-type frame. The lens-frame boundary 52 can extend around a perimeter of the lens 20 (or the perimeters of both lenses in a dual lens system). In such embodiments, one or more engagement portions can be selectively disposed along lower portions, lateral portions, or medial portions (such as adjacent to the nosepiece opening of the lens), and the frame can also comprise corresponding retention components configured to engage the respective engagement portion (s) of the lens(es).

Figure 5:
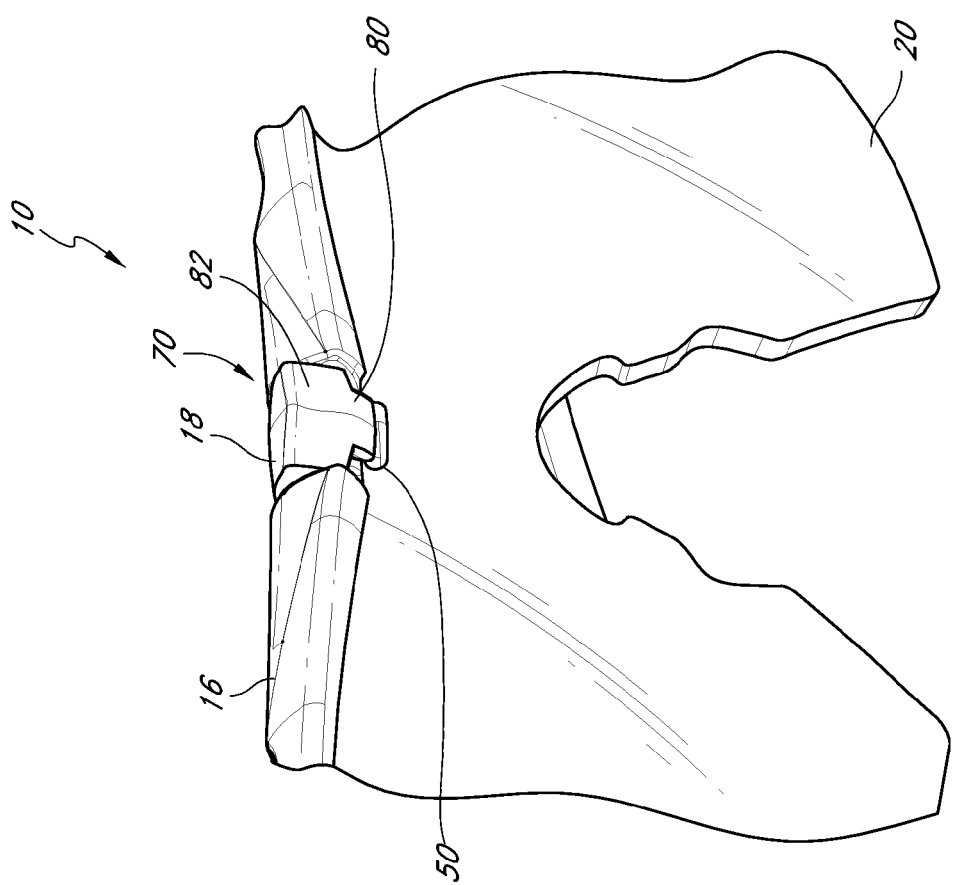
FIG. 5 is an enlarged perspective view of a medial portion of the eyeglass shown in FIG. 1, wherein the retention component is in a disengaged position, according to an embodiment.
Figure 6:
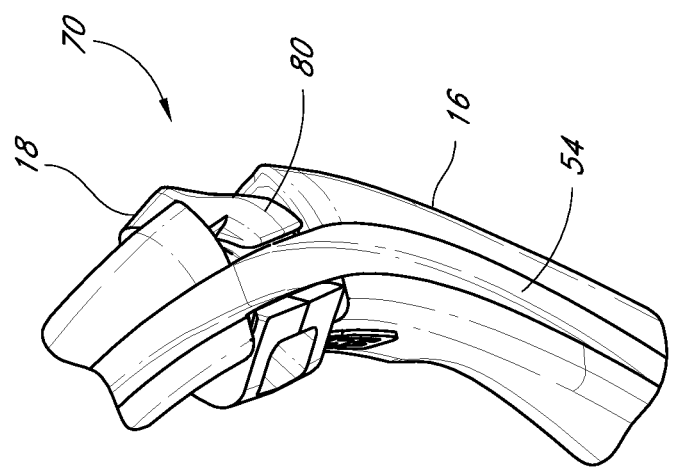
FIG. 6 is a bottom perspective view of a medial portion of the frame, wherein the retention component is in a disengaged position, according to an embodiment.
Figure 7:
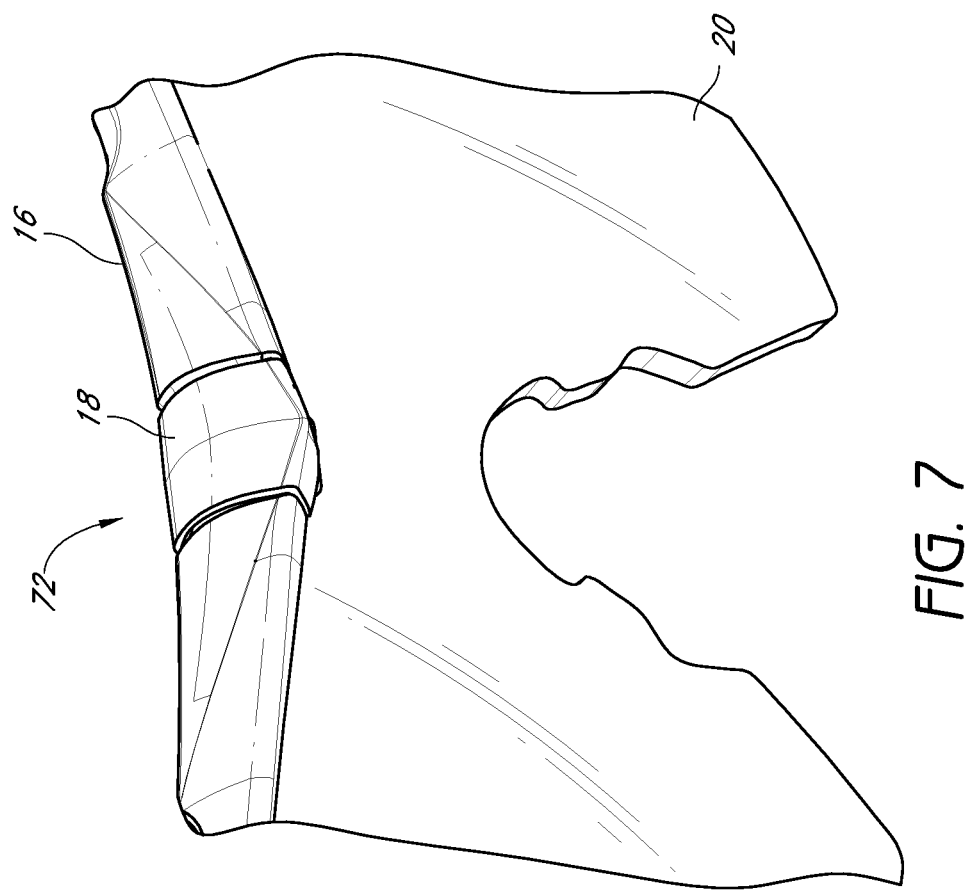
FIG. 7 is an enlarged perspective view of the medial portion of the eyeglass shown in FIG. 1, wherein the retention component is in an engaged position, according to an embodiment.

With reference to FIGS. 5-8, the function and operation of an embodiment of the retention component 18 will now be described. In FIGS. 5-6, the retention component 18 is disposed in a disengaged position 70. Additionally, in FIGS. 7-8, the retention component 18 is disposed in an engaged position 72. As will be appreciated by one skill in the art, when the retention component 18 is disposed in the disengaged position 70, the retention component 18 is not engaged with the corresponding engagement portion 50 of the lens 20. However, when the retention component is disposed in the engaged position 72, the retention component 18 can engage the engagement portion 50 of the lens 20, as shown in FIG. 7.

In order to facilitate engagement with the engagement portion 50 of the lens 20, the retention component 18 can comprise a projection or recess that engages with the corresponding engagement portion 50. As shown in FIGS. 5-8, the retention component 18 can comprise a tab 80 that extends from a body 82 of the retention component 18. In the illustrated embodiment, the tab 80 can be configured to fit within or be seated within the aperture of the engagement portion 50. The tab 80 of the retention component 18 provides an interference engagement to prevent the lens 20 from detaching from the frame 16 or exiting the lens groove 54 of the frame 16.

Figure 8:
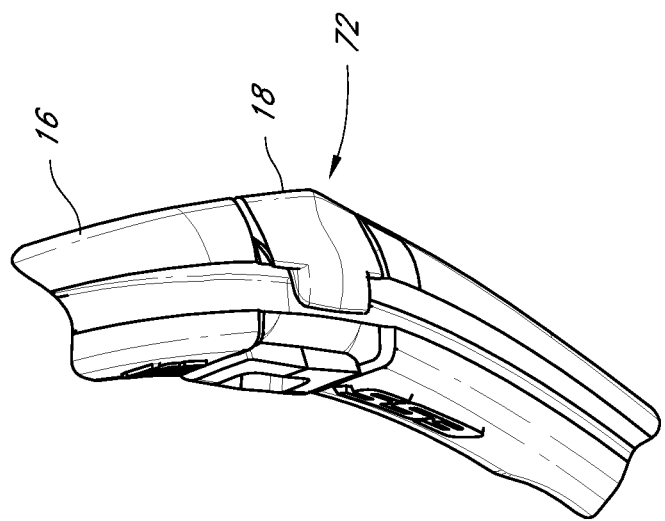
FIG. 8 is a bottom perspective view of the medial portion of the frame, where in the retention component is in an engaged position, according to an embodiment.

As also shown in FIGS. 5-8, in some embodiments, the retention component 18 can be a hingeless clip that defines an outer profile that tapers and blends with the surface of the frame 16. For example, the clip 18 can define a contour or external shape that blends with a contour or external shape of the frame 16. In some embodiments, the contour or external shape can blend in only one of the first or second rotational positions. For example, (as shown in FIGS. 5-6) a mismatch in contour can provide a visible and tactile indication that the clip 18 is in a disengaged position while the clip 18 and frame 16 have a generally uniform, smooth contour when the clip is in the engaged position (as shown in FIGS. 7-8).

Referring to FIGS. 9-11B, embodiments of the retention component 18 are shown as a rotatable component that is coupled to the frame 16. The body 82 of the retention component 18 can be configured as a generally annular or tubular shape that wraps around at least a portion of the frame 16. For example, the body 82 can be configured as a split ring (as visible in the side views of FIGS. 9-11) that encompasses or surrounds a portion of the frame 16. The retention component 18 can wrap around, for example, at least about 50% and/or less than or equal to about 80% of the perimeter or circumference of a portion of the frame 16, with at least about 20% and/or less than or equal to about 50% of the retention component 18 defining a gap or split 90.

Further, the gap or split 90 can be configured such that at least a portion of the lens can be received therein for securing the lens relative to the frame 16. Thus, when rotated to the disengaged position 70, the gap or split 90 can align with a portion of the frame 16, such as the groove 54. As a result, the retention component 18 can allow passage of at least a portion of the lens 22 into the groove 54 of the frame 16. Furthermore, in the embodiments shown in FIGS. 5-11B, the tab 80 can be disposed at one of the free ends forming the gap or split 90. The retention component 18 can be rotated from the first rotational position or disengaged position to the second rotation position or engaged position in which the tab 80 and gap or split 90 is rotated such that the tab 80 of the retention component 18 engages a portion of the lens. Rotation of the gap or split can enable quick and secure engagement with the lens.

In some embodiments, the retention component 18 can be configured to snap-fit onto the frame 16. In embodiments wherein the retention component is a clip 18, the clip can be urged onto the frame 16 with a portion of the frame 16 passing through the gap or split 90 in the clip. In some embodiments, the clip can be fabricated from a resilient material such that the clip deflects to allow enlargement of the gap or split 90 such that the clip can attach to the frame 16. The clip can therefore be attachable to the frame 16 without requiring pins, latches, or other components. Embodiments disclosed herein can thus allow for superior assembly and maintenance of the eyeglass compared to other designs. Further, the design can be durable and sturdy, providing capable and secure retention despite stresses or other forces that may act on the eyeglass.

In some embodiments, the retention component 18 can be configured to be mounted to the lens 22 such that the retention component 18 engages a corresponding retention structure in the frame 16 when the lens 22 is mounted onto the frame 16. For example, the retention component 18 can be mounted such that the retention component 18 is movable relative to the lens 22. However, the retention component 18 can be fixed relative to the lens 22. The retention component 18 can be permanently mounted to the lens 22. The retention component 18 can be detachably mounted to the lens 22. Accordingly, in some embodiments, it is not necessary for the clip or retention component 18 to be part of or carried or supported by the frame 16. The various embodiments and features discussed herein with respect to the retention component 18 in embodiments wherein the retention component 18 is carried or supported by the frame 16 can be incorporated into embodiments wherein the retention component 18 is mounted onto the lens 22.

Figure 10:
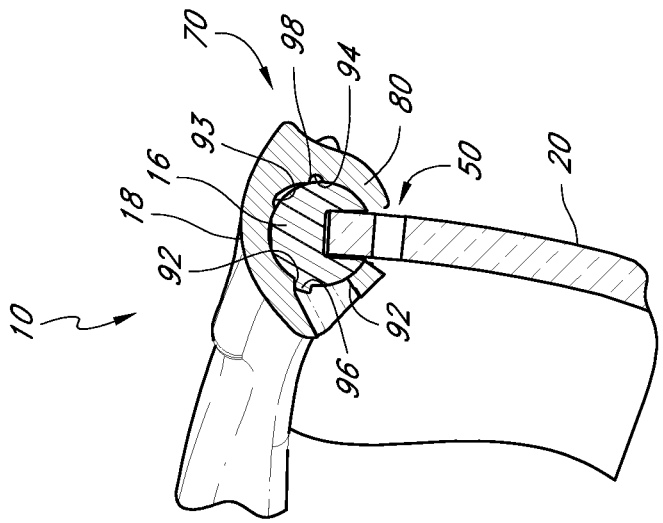
FIG. 10 is a cross-sectional side view of the frame, the retention component, and the lens, wherein the retention component is in the disengaged position and the lens is seated within a groove of the frame, according to an embodiment.

As shown in FIG. 10, the lens 20 can be seated within the groove 54 of the frame 16 when the retention component 18 is positioned in the disengaged position 70. Next, when the retention component 18 is rotated to the engaged position 72, as shown in FIG. 11, the tab 80 of the retention component 18 is advanced to a position within the aperture of the engagement portion 50 of the lens 20. As a result, the lens 20 can be generally constrained from movement in all directions at the point of engagement with the frame 16 in the retention component 18.

For example, the eyeglass 10 can tend to provide superior ballistic resistance and lens stability during use. Further, embodiments of the eyeglass can be provided in which one or more retention components are utilized to attach the lens to the frame. In such embodiments, the lens can be coupled to the frame in a matter that does not distort the lens or undermine its optical qualities. As a result, embodiments of the eyeglass disclosed herein can not only provide superior ballistic resistance and lens stability, but can also provide superior optical quality.

Figure 9:
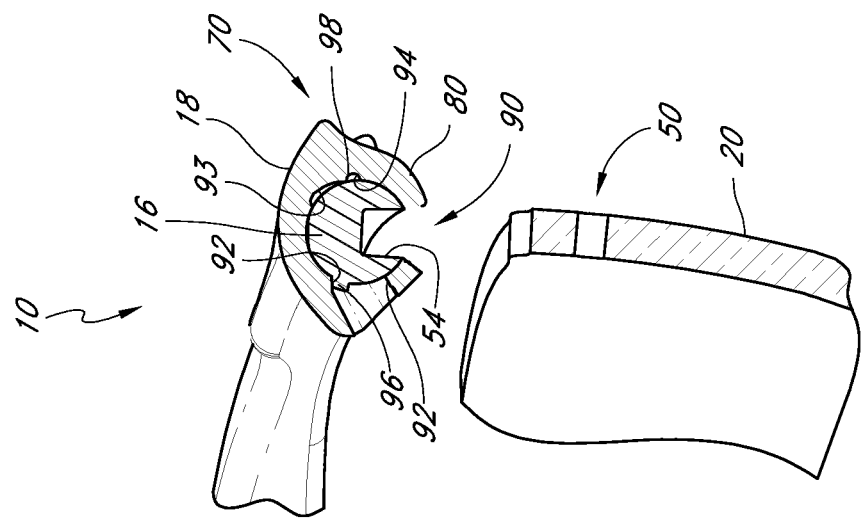
FIG. 9 is a cross-sectional side view of the frame, the retention component, and the lens, wherein the retention component is in the disengaged position and the lens is separated from the frame, according to an embodiment.
Figure 11A:
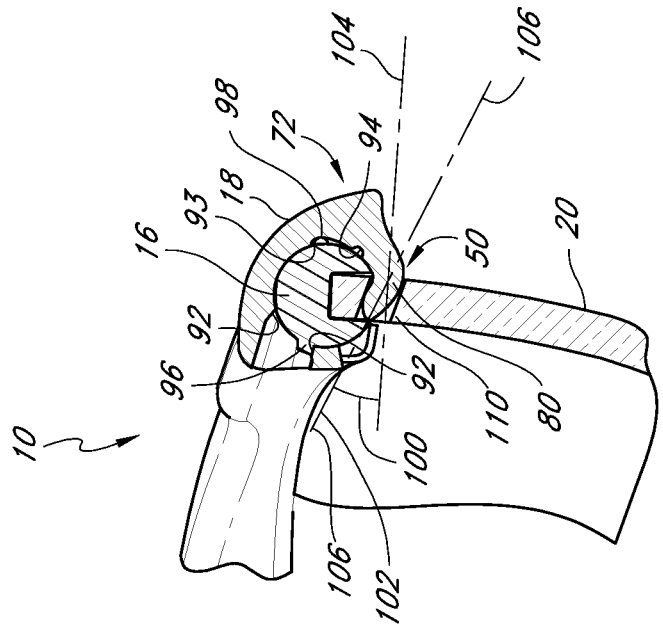
FIG. 11A is a cross-sectional side view of the frame, the retention component, and the lens, wherein the retention component is in the engaged position with the lens being seated within the groove of the frame such that the retention component engages the lens, according to an embodiment.
Figure 11B:
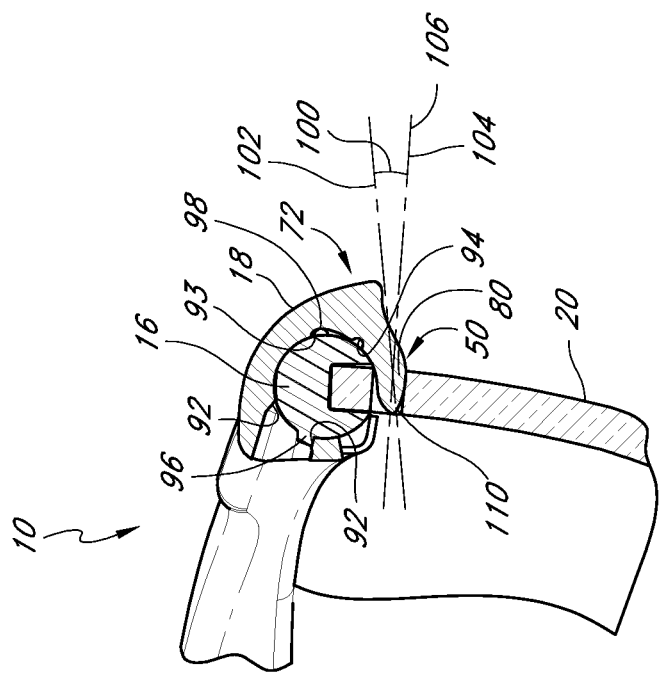
FIG. 11B is a cross-sectional side view of the frame, the retention component, and the lens, wherein the retention component is in the engaged position with the lens being seated within the groove of the frame such that the retention component engages the lens, according to another embodiment.

Additionally, as shown in the embodiments of FIGS. 9-11B, the eyeglass can comprise a motion constrain mechanism. For example, the retention component 18 can comprise one or more stop elements that are configured to interact with one or more stop elements of the frame 16. For example, the retention component 18 can comprise posterior stop elements 92 and upper and lower anterior stop elements 93, 94 that are configured to interact with respective ones of a posterior stop element 96 and an anterior stop element 98 of the frame 16. As illustrated in FIGS. 9-11, the stop elements 92, 93, 94, 96, 98 can restraint rotational movement of the retention component 18 relative to the frame 16. For example, the use of stop elements 92, 93, 94, 96, 98 can facilitate accurate movement from the disengaged position 70 the engaged position 72 and vice versa. Further, in some embodiments, the stop elements 92, 93, 94, 96, 98 can also be used to lock the retention component 18 relative to the frame 16 such that relative rotational movement is prevented. Such a feature can be advantageous once the retention component 18 is moved to the engaged position 72 where it can be snapped into place or otherwise retained to prevent inadvertent disengagement.

In the illustrated embodiment, the frame 18 comprises a pair of stop elements 96, 98 formed as protrusions extending from an outer surface of the bridge portion of the frame 16. Although two stop elements 96, 98 are shown, a single stop element can also be used. Further, in embodiments where two stop elements are used, the stop elements can provide different functions for the retention component 18.

For example, the posterior stop element 96 can be relatively larger than the anterior stop element 98 and primarily provide a restraint against rotation in a given direction. The anterior stop element 98 can provide an engagement function that tends to constrain or substantially fix the rotation position of the retention component 18. The posterior stop element 96 can tend to constrain the rotational position of the retention component 18.

In use, with some initial effort to overcome the engagement between the lower, anterior stop element 98 and the lower, anterior stop element 94 of the retention component 18, the retention component 18 can move from the first rotational position or disengaged position 70. The retention component 18 can continue to rotate until being rotationally constrained or stopped by the posterior stop element 96 and the anterior stop element 92. Further, the retention component 18 can be substantially constrained at the second rotational position or engaged position 72 due to engagement between the anterior stop element 98 and the upper, anterior stop element 93. Although the illustrated embodiment shows at least two stop elements of the retention component 18 interacting with at least two stop elements of the frame 16, the motion constraint mechanism can comprise a single stop on the frame and a single stop on the retention component; the stops can interact to provide rotational restraint and substantial fixation of the rotational position.

Therefore, in such embodiments in which the retention component 18 comprises a hingeless clip, the clip can rotate between two or more rotational positions with hardstop features or stop elements 92, 93, 94, 96, 98 of the clip and the frame 16 restraining motion of the clip at one or more of the positions. As shown, the retention component 18 can comprise an interior surface having one or more recesses 92 that engage with one or more protrusions 94 of the frame 16. Further, the retention component 18 can comprise an interior surface having one or more protrusions that engage with one or more recesses of the frame 16. In some embodiments, the hardstop features can be hidden from view when in an assembled state. Further, engagement between the hingeless clip and the frame can also create the desired interaction between the corresponding hardstop features of the clip and the frame.

Although FIGS. 9-11B illustrate embodiments of the retention component 18 as being rotatable relative to the frame 16, the retention component 18 can be configured to pivot or slide relative to the frame 16. In some embodiments, the retention component 18 could be pivotally coupled to a portion of the frame 16. However, in the illustrated embodiment, the retention component 18 is configured to rotate around the frame 16 in order to allow the tab 80 to engage the engagement portion 50 of the lens 20.

Further, the retention component 18 can comprise a resilient material, such as a compressible or flexible material disposed at least along the tab 80 of the retention component 18. As a result, a ballistic event will not tend to result in damage at the interconnection between the retention component 18 and the engagement portion 50. In such embodiments, the tab 80 can be formed from such a resilient or flexible material or comprise a coating, layer, or one or more surface features formed from the resilient or flexible material. The retention component 18, such as the tab 80 and/or the resilient or flexible material, can have a modulus of elasticity that is less than that of the lens. Further, retention component 18, such as the tab 80 and/or the resilient or flexible material, can have a modulus of elasticity that is less than that of the frame. Accordingly, at least a portion of the retention component 18 can dampen or absorb force or vibration from a ballistic event.

Further, the retention component 18 can be configured such that during rotation of the retention component 18 and engagement with the engagement portion 50 of the lens 20, the lens 20 can be brought into the groove 54 to secure the lens 20 within the groove 54. Such a feature can be facilitated using a cam-like motion of the retention component 18 or a cam-like interaction between the tab 80 and the engagement portion 50.

In some embodiments, the tab 80 of the retention component 18 can engage the engagement portion 50 of the lens 20 in the engaged position (as shown in FIGS. 11A-11B) at a desired engagement angle 100 configured to maximize stability, retention, and resilience of the eyeglass in response to a ballistic event.

The engagement angle 100 can be defined as the angle measured between the tab 80, such as a longitudinal or circumferential centerline or tab axis 102, and a line 104 that is normal to the lens 20. The normal line 104 can be the line that is normal to the lens 20 at approximately the engagement portion 50 of the lens 20.

In some embodiments, the line 104 can be generally parallel with the axis 106 of the engagement portion 50, as shown in the embodiment of FIG. 11A. Further, in some embodiments, the tab axis 102 can be generally parallel with a longitudinal centerline or axis 106 of the engagement portion 50 of the lens 20. For example, as shown in the embodiment of FIG. 11B, the tab axis 102 can be generally parallel with the axis 106 of the engagement portion 50 and oriented transversely relative to the normal line 104 of the lens 20.

The engagement angle 100 can be oriented to ensure optimal retention of the lens 20 relative to the frame 16. For example, in either of the embodiments shown in FIGS. 11A-11B and other embodiments, the engagement angle 100 can be at least about 5 degrees and/or less than or equal to about 40 degrees relative to a horizontal plane. Further, in some embodiments, the tab 80 can engage the engagement portion of the lens at an engagement angle 100 of at least about 10 degrees and/or less than or equal to about 30 degrees relative to a horizontal plane. In some embodiments, the engagement angle 100 can be approximately 12 degrees. In other embodiments, such as the embodiment of FIG. 11B, the engagement angle 100 of approximately 19.2 degrees has been found to provide excellent results in ballistic testing.

Furthermore, the rotational range of the retention component 18 between the engaged and disengaged positions can be at least about 10 degrees and/or less than or equal to about 180 degrees. For example, as shown in FIGS. 10-11B, the retention component 18 can rotate about 45 degrees from the engaged position to the disengaged position.

In some embodiments, the tab 80 retention component 18 can engage the engagement portion 50 of the lens 20 with a leading end 110 of the tab 80 extending through the engagement portion 50. For example, FIGS. 11A-B illustrates that the leading end 110 extends to the other face or through the width of the lens 20. However, the leading end 110 can extend only partially into the engagement portion 50 or beyond the engagement portion 50. For example, the leading end 110 can extend through the engagement portion 50 at least about 5 degrees and/or less than or equal to about 90 degrees. Thus, the leading end 110 can be rotated down from the frame 16, through the lens 20, and back toward the frame 16. In some embodiments, the leading end 110 can snap fit or engage the frame 16 to reach a locked fit in the engaged position.

Figure 12:
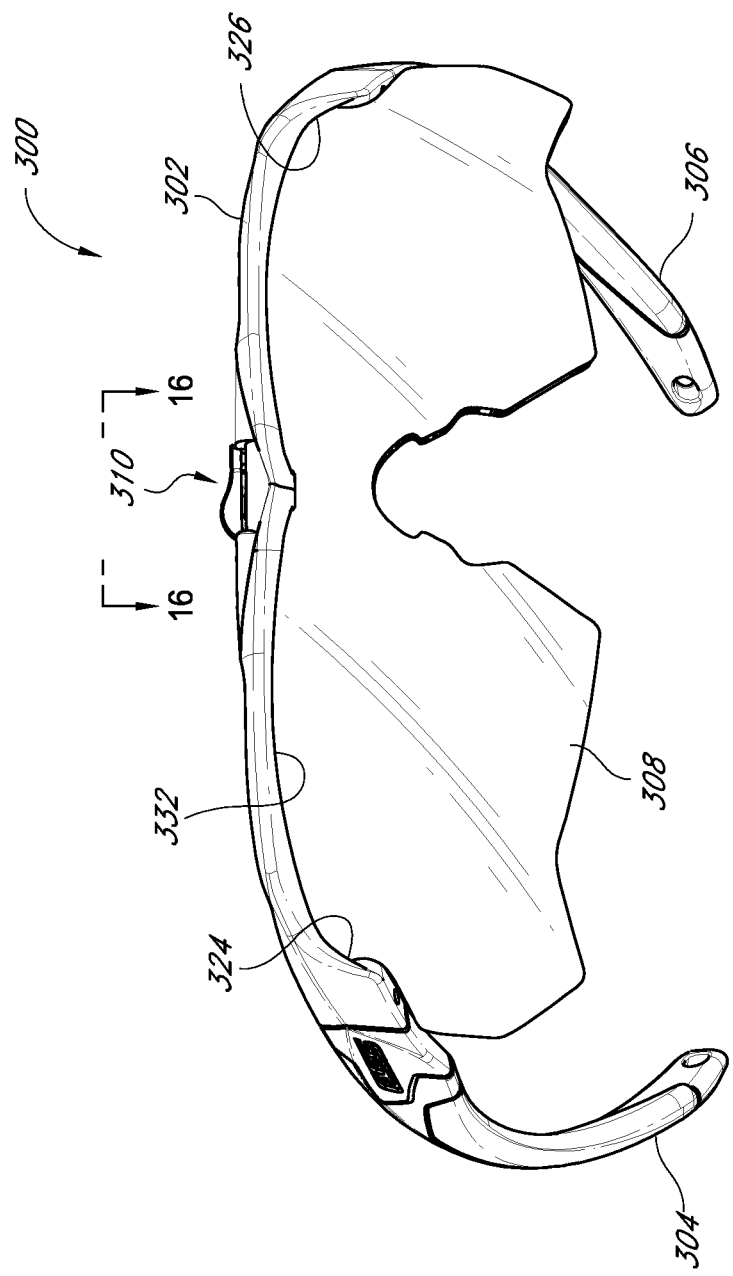
FIG. 12 is a perspective view of an eyeglass comprising a retention component for securing a lens to a frame of the eyeglass, in accordance with another embodiment.

Referring now to FIGS. 12-19, another embodiment of an eyeglass having a retention mechanism is shown. FIG. 12 is a perspective view of an eyeglass 300 that comprises a frame 302, a pair of ear stems 304, 306 extending rearwardly from the frame 302, a lens 308, and a retention mechanism 310. In this embodiment, the retention mechanism 310 can be concealed within the frame 302 such that the eyeglass 300 maintains the appearance of a conventional eyeglass while exhibiting excellent ballistic properties.

Figure 13:
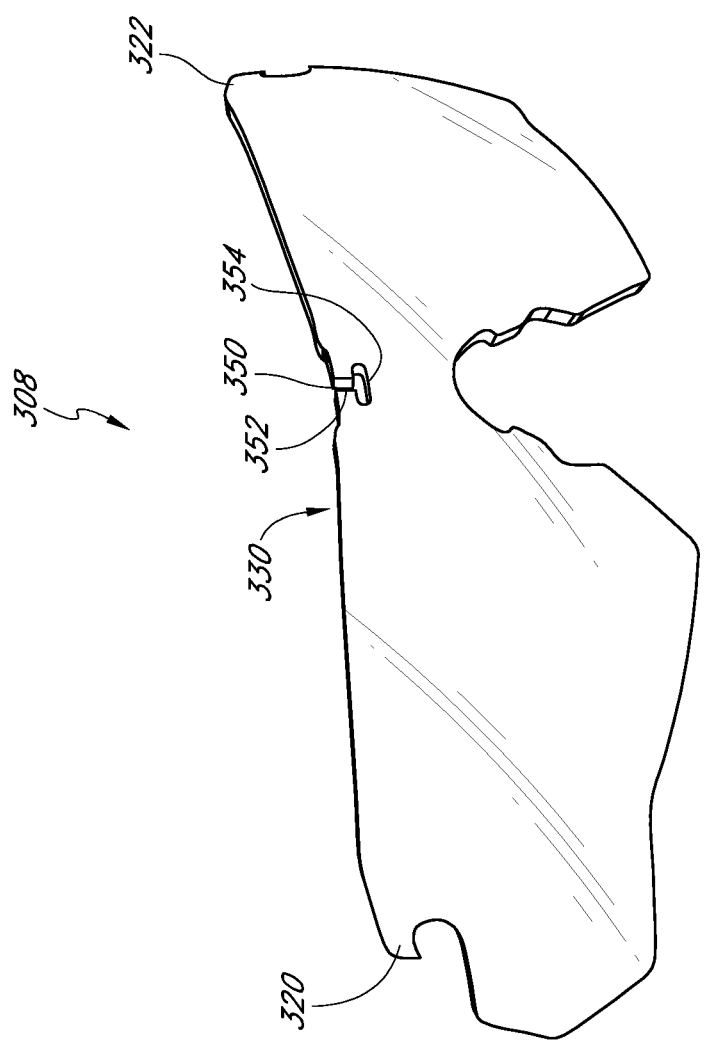
FIG. 13 is a perspective view of a lens comprising a slot that can be engaged and/or supported by the retention component of the eyeglass shown in FIG. 12, according to an embodiment.

FIG. 13 illustrates an embodiment of a lens 308 for use with an eyeglass. The lens 308 can be configured to be supported by the frame 302. For example, the lens 308 can comprise one or more engagement portions that can be engaged with one or more retention components of the eyeglass for supporting the lens. Further, other structures can be used to support the lens. For example, the frame can comprise one or more opposing terminals and the lens can comprise one or more projections that can be fitted into the terminal(s) of the frame. However, the use of structures such as projections and terminals is optional and can be omitted in some embodiments. For example, structures in addition to the retention component(s) and engagement portion(s) may be unnecessary where two or more retention components and engagement portions are spaced apart along the edge of the lens.

In some embodiments, the lens 308 can comprise a pair of projections 320, 322 that can be seated in corresponding terminal recesses 324, 326 of the frame 302. Further, the lens 308 can comprise an upper edge or boundary 330. In use, when the projections 320, 322 are fitted into the recesses 324, 326 of the frame 302, the upper edge or boundary 330 of the lens 308 can be generally snap-fitted into and retained within a lens groove 332 of the frame 302. Thus, in some embodiments, such an arrangement can provide a further degree of lens retention and stabilization in addition to that provided by the retention component.

In accordance with the embodiment shown in FIGS. 12-19, the lens 308 can also comprise an engagement portion 350. The engagement portion 350 can comprise at least one portion of the lens 308 can be one of a recess, surface contour, cut-out, projection, slot, aperture, and other such surface structures and be formed in a variety of shapes and/or sizes. For example, in the illustrated embodiment, the engagement portion 350 is shown as a cut-out that extends through the thickness of the lens 308. Further, the engagement portion 350 is shown as a single cut-out, but can be formed as a plurality of cut-outs. Additionally, the engagement portion 350 can be formed to comprise a narrowed section 352 and a wide section 354.

Figure 15:
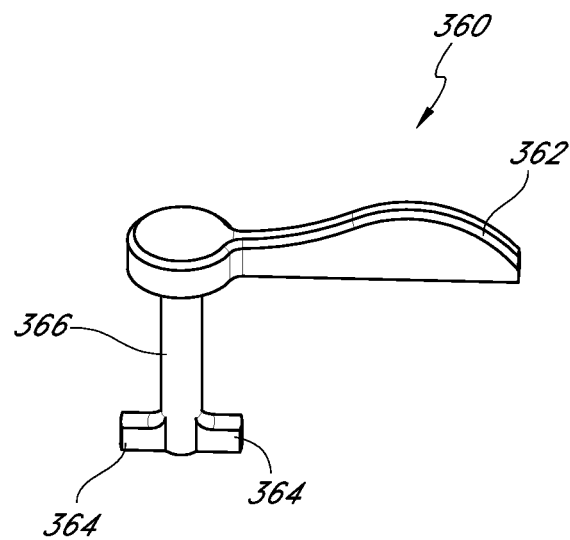
FIG. 15 is a perspective view of the retention component of the eyeglass of FIG. 12, according to an embodiment.

Referring now to FIG. 15, an embodiment of a retention component 360 is shown. The retention component 360 can be configured to engage and secure the lens 308 relative to the frame 302. For example, the retention component 360 can be positioned in one of an engaged position and a disengaged position. In the engaged position, the retention component 360 can interlock, engage, and/or otherwise secure at least a portion of the lens 308 relative to the frame 302. In the disengaged position, the retention component 360 can allow the lens 308 to move freely relative to the frame 302. Further, the retention component 360 can be manually actuated by the wearer in order to allow the wearer to interchange lenses.

In the illustrated embodiment, the retention component 360 can comprise a switch or handle 362 and at least one tab 364. The retention component 360 can be configured to rotate about a generally vertical axis relative to the eyeglass 300. The handle 362 can be actuated by the wearer. In some embodiments, the retention component 360 can comprise an elongate shaft 366 extending between the handle 362 and the tab 364. Further, some of us can be configured such that the retention component 360 comprises a pair of tabs 364. As shown, the tab(s) 364 can extend in generally opposite horizontal directions and be attached to a lower or bottom end of the retention component 360.

Figure 17:
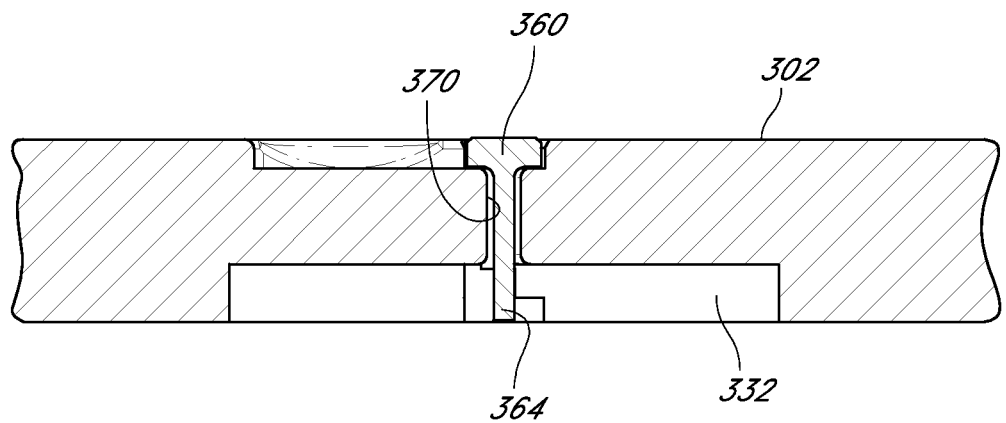
FIG. 17 is a cross-sectional front view of the frame and retention component of the eyeglass of FIG. 12, wherein the retention component is in a disengaged position, according to an embodiment.
Figure 18:
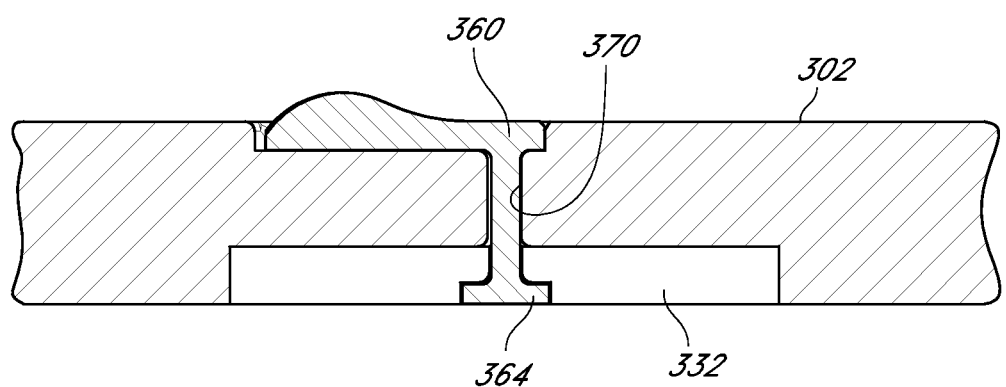
FIG. 18 is a cross-sectional front view of the frame and retention component of the eyeglass of FIG. 12, wherein the retention component is in an engaged position, according to an embodiment.
Figure 19:
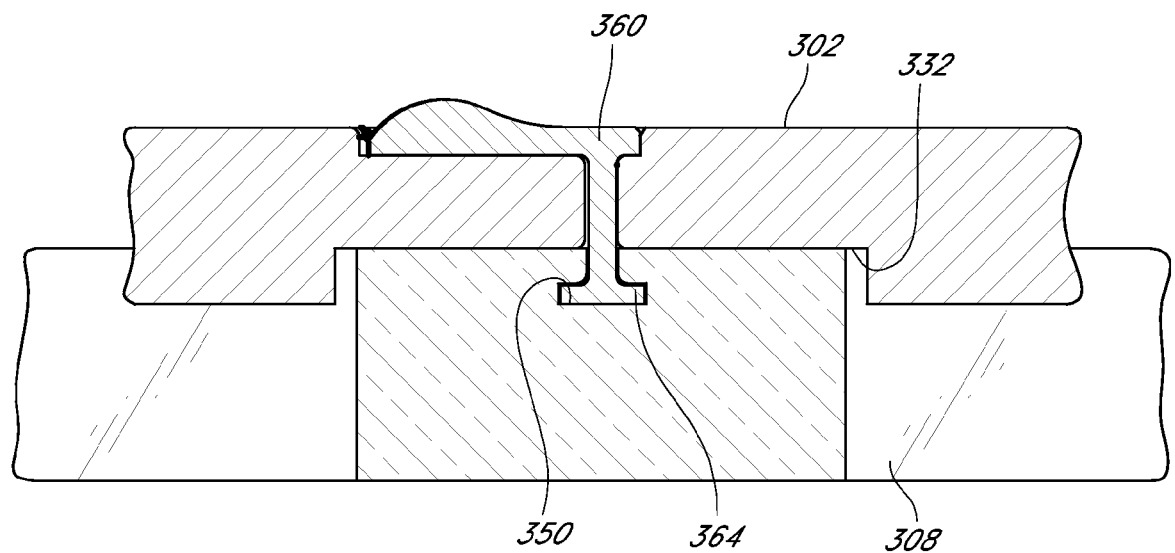
FIG. 19 is a cross-sectional front view of the frame and retention component of the eyeglass of FIG. 12, wherein the retention component is in the engaged position and engaging the lens, according to an embodiment.

The tab 364 can be disposed adjacent to the lens 308 for engaging the lens 308 such that the tab 364 can be positioned in an engaged position or a disengaged position relative to the lens 308 for engaging lens 308. The engaged and disengaged positions of the retention component 360 relative to the frame 302 are shown in FIGS. 17 and 18. Further, FIG. 19 illustrates the retention component 360 engaging the lens 308 in the engaged position.

Figure 14:
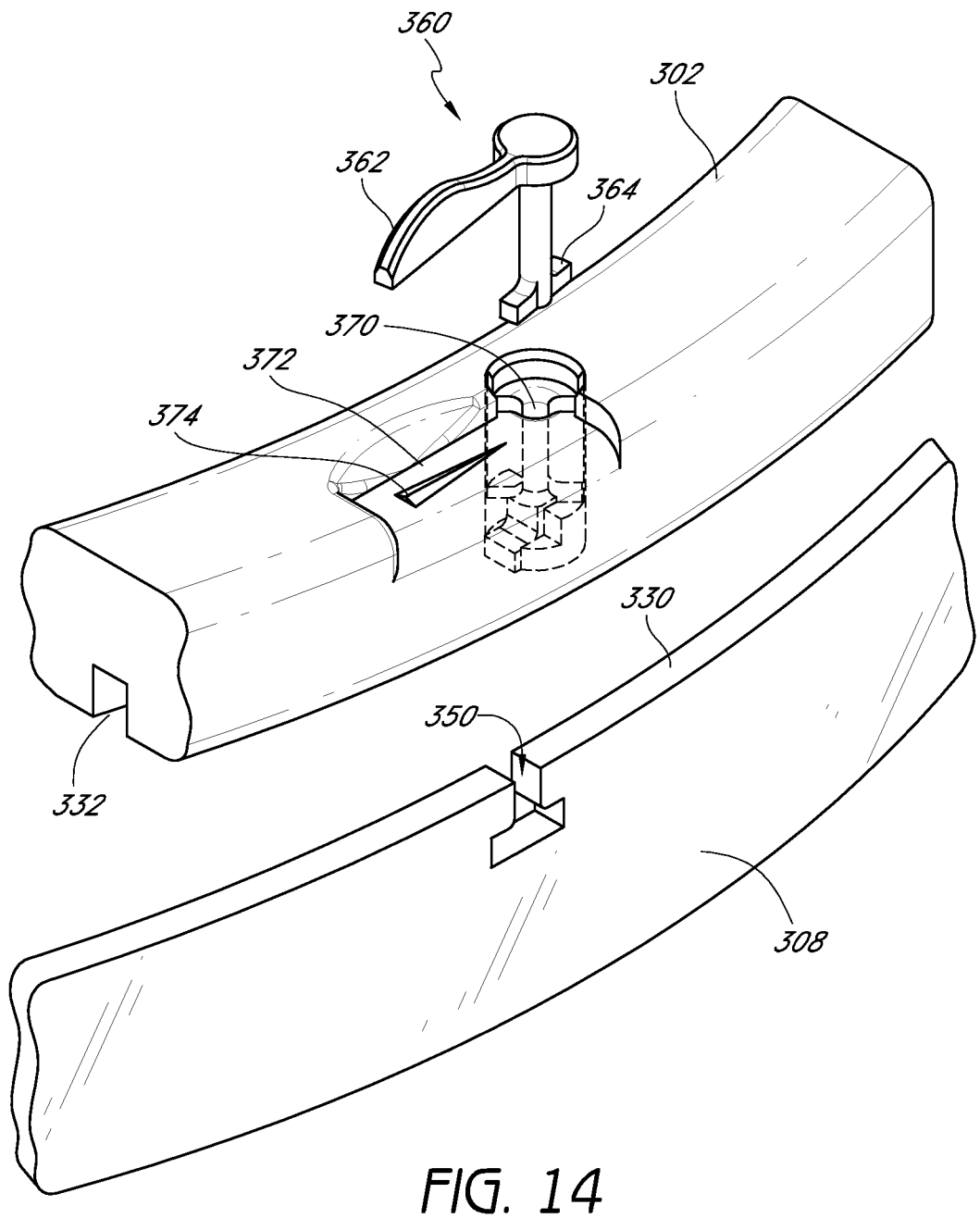
FIG. 14 is a perspective view of another eyeglass, frame, and retention component according to another embodiment.
Figure 16:
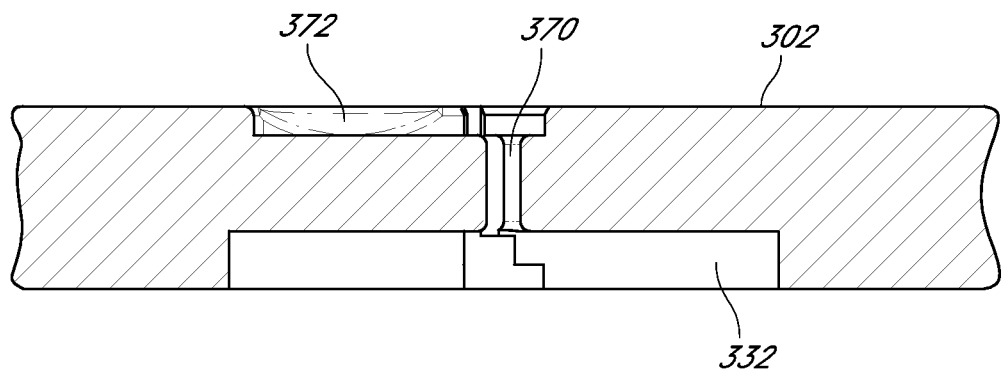
FIG. 16 is a cross-sectional front view of the frame of the eyeglass of FIG. 12, illustrating a recess configured to support the retention component shown in FIG. 15, according to an embodiment.

FIG. 14 is an enlarged perspective view of the eyeglass 300 and the retention mechanism 310. FIG. 16 is a cross-sectional front view of the frame 302 of the eyeglass 300 taken along lines of FIG. 12. As illustrated, the frame 302 can comprise a recess 370 configured to support the retention component 360 shown in FIG. 15, according to an embodiment. FIG. 16 also illustrates the lens groove 332 extending along the frame 302. The recess 370 can be configured to allow the tab 364 of the retention component 360 to be passed downwardly toward the lens groove 332. Further, the recess 370 can comprise a handle-receiving section 372 at an upper end thereof for accommodating at least a portion of the handle 362 of the retention component 360. As shown in FIG. 14, the recess 370 can comprise a rotational step-wise distribution of gaps. The gaps can be configured to allow the tab(s) 364 of the retention component 360 to be rotated as it is advanced into the recess 370, which rotation can limit axial or vertical movement of the retention component 360 (and unintentional removal of the retention component 360 from the recess 370). In this manner, the retention component 360 can be securely seated into and retained by the recess 370. In use, the recess 370 can allow the retention component 360 to rotate therein with the handle 362 being pivotable within the section 372 of the recess 370. Further, the frame 302 can comprise a bump 374 that provides interference and/or frictional resistance to movement of the handle 362 thereover. Thus, unintentional rotation and disengagement of the retention component 360 can be generally prevented.

Additionally, as shown in FIGS. 17 and 18, when the retention component 360 is disposed in the recess 370, the tab 364 can be positioned within or extend within the lens groove 332. Accordingly, the tab 364 can be rotated such that the retention component 360 is in the disengaged position, as shown in FIG. 17. When the retention component 360 is in the disengaged position, the lens 308 can be positioned within the lens groove 332 with the tab 364 fitting into the narrowed section 352 of the engagement portion 350 of the lens 308. Further, as shown in FIG. 19, the retention component 360 can be rotated to the engaged position such that the at least one tab 364 rotates to fit within the widened section 354 of the engagement portion 350 of the lens 308. The retention component 360 can thus be rotated in a plane that is generally coplanar with the engagement portion 350 of the lens. Thus, the retention component 360 can rotate within the engagement portion 350 of the lens 308 in order to selectively engage or disengage with the lens.

The embodiment shown in FIGS. 12-19 enables the retention component 360 to interlock or couple the lens 308 relative to the frame 302. Notably, with the upper edge or boundary 330 of the lens 308 being fitted into the lens groove 332 and with the tab 364 engaging the engagement portion 350 of the lens 308, the lens 308 can be generally constrained against translational and rotational movement with respect to the frame 302. The ballistic strength of the eyeglass can be substantially increased with such a design.

The retention component taught herein can provide excellent ballistic resistance for the lens and the frame of the eyeglass. The retention component can be integrated into, carried, or supported by the frame of the eyeglass. The retention component can also be integrated into, carried, or supported by the lens or lenses supported by the frame. The retention component can also be formed as a separate part that can be retrofitted onto existing eyewear. In some embodiments, the retention component can restrict rotational and/or translational movement of the lens relative to the frame at one or more points of the engagement between the lens and the frame. Further, the retention component can comprise a portion of the frame and/or a portion formed separately from the frame that engages with a portion of the lens.

Some of the embodiments discussed herein provide for a retention component that performs the function of engaging the frame separately from the function of engaging the lens. However, the retention component can engage both the frame and the lens together. For example, the retention component can engage a protrusion of the frame onto which the lens is mounted, thus engaging the frame and engaging and restricting movement of the lens.

Embodiments of the eyeglass disclosed herein can tend to ensure that the lens does not become substantially separated from the frame in response to a ballistic event. Further, embodiments of the eyeglass can be configured such that any force transmitted to the lens is also transmitted to the frame of the eyeglass while substantially maintaining engagement between the lens and the frame. For example, although the lens of such an eyeglass may be damaged (cracked or chipped), the lens may not be shattered or displaced relative to the frame. This ballistic resistance can provide excellent protection to the wearer.

Additionally, the retention component can comprise a resilient material, such as a compressible or flexible material disposed at least along a portion of the retention component. For example, a tab, connector, body, or other structure or component of the retention component can be formed from and/or include one or more resilient materials. As a result, a ballistic event will not tend to result in damage at the interconnection between the retention component and the engagement portion. In some embodiments, a tab of the retention component can be formed from a resilient or flexible material or comprise a coating, layer, or one or more surface features formed from the resilient or flexible material. The retention component, such as the tab and/or the resilient or flexible material, can have a modulus of elasticity that is less than that of the lens. Further, retention component, such as the tab and/or the resilient or flexible material, can have a modulus of elasticity that is less than that of the frame. Accordingly, at least a portion of the retention component can dampen or absorb force or vibration from a ballistic event.

The eyeglass can comprise a plurality of retention components that engage the lens and/or the frame to secure the lens relative to the frame. For example, a lens of the eyeglass can be engaged and/or supported at two or more points along the upper edge or boundary thereof.

In an embodiment that comprises a unitary lens, the lens can be engaged and/or supported at least at both lateral sides and a central portion thereof. For example, a unitary lens may be secured to and/or supported by a frame using a first retention structure on the left side of midline and a second retention structure on the right side of midline. The retention structures can include any of the clips or other mechanisms disclosed herein. The first retention structure may be centered on a point that is within the left lateral one third of the length of the frame, measured hinge to hinge. The second retention structure may be centered on a point that is within the right lateral one third of the frame. A third retention structure may also be used, located within the central one third of the frame, preferably on the midline. Four or five or more retention structures may also be used, depending upon the desired performance. Typically, the retention structures can be symmetrically spaced apart along the length of the frame, or as a mirror image across the plane of symmetry (anatomical midline).

In an embodiment that comprises dual lenses, each lens can be engaged and/or supported by at least one retention component. For example, a dual lens may be secured to and/or supported by the frame using a first retention structure on the left side of a midline and a second retention structure on the right side of the midline. In some embodiments, a dual lens can be secured by three or more retention components, for example, at both lateral sides and a central portion thereof. Alternatively, a dual lens may be secured by a single retention component and by engagement between the dual lens and the frame, such as with a protrusion, catch, or tab that engages a recess of the frame. As with the unitary lens embodiments discussed above, typically, the retention structures can be symmetrically spaced apart along the length of the frame, or as a mirror image across the plane of symmetry (anatomical midline).

Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

What is claimed is:

1. An eyeglass comprising:
a frame configured to support at least one lens in a field of view of a wearer, the frame comprising a first ear stem and a second ear stem, the frame being configured to be worn on the wearer's head; and
at least one hingeless retention component being mounted on a top portion of the frame, the retention component being movable relative to the frame and relative to the lens to secure an engagement portion of the lens for preventing the lens from separating from the frame in response to a ballistic event.

2. An eyeglass as in claim 1, wherein the retention component rotates relative to the frame to secure the lens.

3. An eyeglass as in claim 2, wherein the retention component rotates about a generally horizontal axis relative to the frame to secure the lens.

4. An eyeglass as in claim 3, wherein the retention component comprises a rotatable clip comprising an engagement structure that is operative to secure the engagement portion of the lens.

5. An eyeglass as in claim 4, wherein the rotating clip comprises a generally tubular body and the engagement structure comprises an engagement tab extending generally circumferentially relative to the tubular body, the tubular body being configured to engage a recess of the frame for mounting the retention component on the frame, the tab having a first orientation in which the lens is movable relative to the frame and a second orientation in which the tab secures the lens relative to the frame.

6. An eyeglass as in claim 5, wherein the tab of the clip secures the lens at an angle of at least about 5 degrees and/or less than or equal to about 40 degrees relative to a horizontal plane.

7. An eyeglass as in claim 6, wherein the tab of the clip secures the lens at an angle of about 19.2 degrees relative to a horizontal plane.

8. An eyeglass as in claim 4, wherein the retention component is a split ring.

9. An eyeglass as in claim 4, wherein the retention component fits over a recess of the frame to be rotatable about a longitudinal axis of the frame.

10. An eyeglass as in claim 9, wherein the retention component fits over the recess in a snap fit.

11. An eyeglass as in claim 4, wherein the engagement portion of the lens comprises one of a recess and an aperture that can be secured by the engagement structure of the rotating clip.

12. An eyeglass as in claim 1, wherein the retention component comprises a clip disposed at a central portion of the frame, the clip being moveable by the wearer to secure a central portion of the lens to the frame.

13. An eyeglass as in claim 1, wherein the frame comprises opposing lateral terminals that interconnect with corresponding projections in the lens to mount the lens to the frame in a mounted position.

14. An eyeglass comprising:
   at least one lens comprising an engagement portion;
   a frame having a generally horizontal longitudinal axis and a pair of earstems extending posteriorly relative to the frame, the frame being configured to support the at least one lens in the field of view of a wearer; and
   at least one hingeless retention mechanism being coupled to a top portion of the frame and rotatable about the longitudinal axis of the frame, the retention mechanism comprising an engagement structure extending therefrom, the engagement structure being moveable from a first orientation in which the lens can be freely moved relative to the frame to a second orientation in which the retention structure engages the engagement portion of the lens for securing the lens relative to the frame.

15. An eyeglass as in claim 14, wherein the frame comprises at least one stop element configured to limit the rotational orientation of the retention mechanism relative to the frame.

16. An eyeglass as in claim 15, wherein the retention mechanism comprises at least one stop element corresponding to the at least one stop element of the frame, the stop elements being configured to contact each other to limit the rotational orientation of the retention mechanism relative to the frame.

17. An eyeglass as in claim 16, wherein the retention mechanism comprises first and second stop elements that interact with the at least one stop element of the frame.

18. An eyeglass as in claim 16, wherein the retention mechanism has a generally tubular body with the engagement structure extending generally circumferentially therefrom.

19. An eyeglass as in claim 18, wherein the at least one stop element of the retention mechanism is formed along an interior surface of the retention mechanism.

20. An eyeglass as in claim 16, wherein the at least one stop element of the retention mechanism comprises a recess and the at least one stop element of the frame comprises a protrusion.

21. An eyeglass as in claim 14, wherein the engagement structure of the retention mechanism comprises a tab that engages the engagement portion of the lens at an angle of at least about 5 degrees and/or less than or equal to about 40 degrees relative to a horizontal plane.

22. An eyeglass as in claim 21, wherein the engagement structure of the retention mechanism comprises a tab that engages the engagement portion of the lens at an angle of about 19.2 degrees relative to a horizontal plane.

* * * * *